US012246060B2

(12) United States Patent
Drewlo et al.

(10) Patent No.: US 12,246,060 B2
(45) Date of Patent: Mar. 11, 2025

(54) IRISIN IMPROVES PLACENTAL FUNCTION DURING PREGNANCY

(71) Applicant: Board of Trustees of Michigan State University, East Lansing, MI (US)

(72) Inventors: Sascha Drewlo, Grand Rapids, MI (US); Hamid-Reza Kohan-Ghadr, Kentwood, MI (US); Eugenia Johnson, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 718 days.

(21) Appl. No.: 17/439,163

(22) PCT Filed: Mar. 13, 2020

(86) PCT No.: PCT/US2020/022733
§ 371 (c)(1),
(2) Date: Sep. 14, 2021

(87) PCT Pub. No.: WO2020/190759
PCT Pub. Date: Sep. 24, 2020

(65) Prior Publication Data
US 2022/0152158 A1 May 19, 2022

Related U.S. Application Data

(60) Provisional application No. 62/819,239, filed on Mar. 15, 2019.

(51) Int. Cl.
*A61K 38/17* (2006.01)
*A61K 9/00* (2006.01)
*A61K 38/22* (2006.01)
*A61K 45/06* (2006.01)

(52) U.S. Cl.
CPC ............ *A61K 38/22* (2013.01); *A61K 9/0019* (2013.01); *A61K 38/1709* (2013.01); *A61K 45/06* (2013.01)

(58) Field of Classification Search
CPC .... A61K 38/1709; A61K 38/22; C07K 14/47; C07K 14/4702; C07K 14/4705; C07K 14/4715
See application file for complete search history.

(56) References Cited

U.S. PATENT DOCUMENTS 5,089,264 A 2/1992 Eiler
2013/0280736 A1 10/2013 Caniggia et al.
2015/0330989 A1 11/2015 Burwick et al.
2016/0058873 A1* 3/2016 Fetzer .................... C08G 69/40
514/12.4
2017/0312339 A1 11/2017 Trujillo et al.

OTHER PUBLICATIONS

Drewlo et al. Irisin induces trophoblast differentiation via AMPK activation in the human placenta. Journal of Cellular Physiology. Feb. 5, 2020, vol. 235, pp. 7146-7158. (Year: 2020).*
I. Khan. Irisin: As a Therapeutic Target for Metabolic Disorders. Journal of Endocrinology and Metabolism. 2018, vol. 8, No. 5, pp. 87-93. (Year: 2018).*
Szumilewicz et al. The Exercise-Induced Irisin Is Associated with Improved Levels of Glucose Homeostasis Markers in Pregnant Women Participating in 8-Week Prenatal Group Fitness Program: A Pilot Study. BioMed Research International. Oct. 31, 2017, vol. 2017, Article ID 9414525, 10 pages. (Year: 2017).*
International Search Report from corresponding PCT Application No. PCT/US2020/022733 dated Jun. 22, 2020.
Written Opinion from corresponding PCT Application No. PCT/US2020/022733 dated Jun. 22, 2020.
International Preliminary Report on Patentability from corresponding PCT Application No. PCT/US2020/022733 dated Sep. 16, 2021.
Garces, M.F., et al., "Irisin Levels During Pregnancy and Changes Associated With the Development of Preeclampsia," J. Clin. Endocrinol. Metab., 99(6): 2113-2119 (2014).
Banek, C.T., et al., "AICAR administration ameliorates hypertension and angiogenic imbalance in a model of preeclampsia in the rat," Am J Physiol Heart Circ Physiol, 304(8): H1159-H1165 (2013).
Tang, H., et al., "Irisin Inhibits Hepatic Cholesterol Synthesis via AMPK-SREBP2 Signaling," EBioMedicine, 6: 139-148 (2016).
UniProtKB Accession No. Q8NAU1, "Fibronectin type III domain-containing protein 5," (2008).
Zhang, L., et al., "Expressions of irisin and urotensin II and their relationships with blood pressure in patients with preeclampsia," Clinical and Experimental Hypertension, 39(5): 460-467 (2017).
Ural, U.M., et al., "Alteration of maternal serum irisin levels in gestational diabetes mellitus," Gynecology, 87(5): 395-398 (2016).
Kumagai, A., et al., "AMP-Activated Protein (AMPK) in Pathophysiology of Pregnancy Complications," Int. J. Mol. Sci., 19: 1-13 (2018).
Lee, H.J., et al., "Irisin, a Novel Myokine, Regulates Glucose Uptake in Skeletal Muscle Cells via AMPK," Mol Endocrinol, 29(6): 873-881 (2015).
Wang, P., et al., "Reduced plasma level of irisin in first trimester as a risk factor for the development of gestational diabetes mellitus," Diabetes Research and Clinical Practice, 142: 130-138 (2018).

* cited by examiner

*Primary Examiner* — Jeffrey E. Russel
(74) *Attorney, Agent, or Firm* — Harness, Dickey & Pierce, PLC

(57) ABSTRACT

A method for treating or inhibiting the progression of placental insufficiency syndrome in a subject in need thereof is provided. The method includes administering to the subject a therapeutically effective amount of a composition including irisin.

19 Claims, 32 Drawing Sheets
(1 of 32 Drawing Sheet(s) Filed in Color)
Specification includes a Sequence Listing.

| Description | pValue |
|---|---|
| Pyrimidine metabolism* | 0.030 |
| Pentose and glucuronate interconversions* | 0.037 |
| Metabolic pathways* | 0.055 |
| Fatty acid elongation* | 0.066 |
| Sulfur metabolism* | 0.066 |

© Advaita Corporation 2019

IRISIN IMPROVES PLACENTAL FUNCTION DURING PREGNANCY

This application is a 371 U.S. National Phase entry of International Application No. PCT/US2020/022733, filed on Mar. 13, 2020, which claims the benefit of U.S. Provisional Application No. 62/819,239, filed on Mar. 15, 2019. The entire disclosures of the above applications are incorporated herein by reference.

REFERENCE TO AN ELECTRONIC SEQUENCE LISTING

This application contains references to amino acid sequences and/or nucleic acid sequences which have been submitted concurrently herewith as the sequence listing .txt file entitled "SL_8_Jul_2024_ST25_ST25.txt", file size 4,000 Bytes (B), created on 8 Jul. 2024. The aforementioned sequence listing is hereby incorporated by reference in its entirety.

FIELD

The present disclosure relates to methods of treating or slowing the progression of placental insufficiency syndrome with irisin.

BACKGROUND

This section provides background information related to the present disclosure which is not necessarily prior art.

The human placenta, a vital organ that supports fetal growth and development during pregnancy, is composed of two distinct compartments. The villous chorion develops through a dynamic balance of cytotrophoblast (CTB) proliferation and differentiation. Syncytial fusion of postmitotic CTB builds and maintains the outer syncytiotrophoblast (STB), the site of nutrient and gas exchange. In parallel, the invasive extravillous trophoblast (EVT) cells migrate and invade the uterine wall and its vasculature to establish the fetomaternal link. During human placental development, trophoblast proliferation and differentiation work in tandem, and any major imbalance can cause trophoblast dysfunction and contribute to disorders such as gestational diseases, preeclampsia, and intrauterine growth restriction. Abnormal trophoblast differentiation occurs in preeclamptic placentas. Insufficient spiral artery remodeling by the invading trophoblast cells reduces uteroplacental perfusion, causing a hypoxic state at the implantation site. In response to the low oxygen level, the placenta secretes proteins into the maternal circulation with a variety of consequences including systematic maternal endothelial dysfunction, proteinuria, and hypertension.

Various proteins, including the glial cells missing-1 (GCM1) transcription factor, regulate the terminal differentiation of villous trophoblasts. GCM1 initiates and maintains the syncytium, partly by direct regulation of the fusogenic protein syncytin-1 (SYN1). Additionally, GCM1 induces differentiation and invasion of the EVT cells. The trophoblast cells acquire these characteristics through repression of cell adhesion proteins, including epithelial cadherin (E-cadherin), and subsequently develop invasive properties through the overexpression of matrix metalloproteinase-9 (MMP-9) and matrix metalloproteinase-12 (MMP-12). Integrin switching is another hallmark of EVT differentiation. During the process toward an invasive phenotype, expression of the $\alpha6\beta4$ integrin becomes undetectable in differentiated EVT cells, whereas the collagen/laminin receptor, integrin $\alpha1\beta1$, is upregulated. It has been shown that antibody perturbation of integrin $\alpha1\rho1$ suppresses EVT differentiation. Since EVT differentiation occurs most extensively in the first trimester when the placenta is exposed to a low oxygen environment, the EVT differentiation process is also derived by oxygen-sensitive signaling pathways, such as the hypoxia-inducible factor (HIF), mammalian target of rapamycin, and adenosine monophosphate-activated protein kinase (AMPK) pathways.

AMPK is a serine/threonine kinase and has an important role in modulating metabolic homeostasis. Activation of AMPK is reported to be associated with low cell proliferation and negative regulation of cell cycle modulators, such as cyclin-dependent kinases, cyclin D3, cyclin E1, and proliferating cell nuclear antigen. Active AMPK is also reported to contribute to placental differentiation. Suppressing AMPK results in the failure of mouse placental labyrinthine trophoblast differentiation because of reduced glycolysis and metabolic alterations. In hypoxia, AMPK inactivation in the human placenta causes malfunction via an increasing plasma level of sFlt-1 that results in angiogenic imbalance. In preeclampsia, AMPK activators ameliorate some symptoms.

Irisin is a hormone primarily known to be secreted by myocytes. With 112 amino acid residues, irisin is proteolytically cleaved from fibronectin type Ill domain-containing 5 (FNDC5). The activation of peroxisome proliferator-activated receptor-γ coactivator-1a regulates the release of irisin from skeletal muscle. Irisin has an important role in thermogenesis and energy homeostasis and induces glucose homeostasis. Irisin is positively correlated with body mass index, muscle, and fat masses. Adipokinesis and neurokinesis are also related to irisin function. In addition to metabolic activity, irisin shows a lineage-specific regulation of differentiation in bone marrow by promoting osteoblastogenesis and preventing differentiation of osteoclasts. Similarly, the overexpression of FNDC5 increases neural differentiation and expression of the neuroprotective marker brain-derived neurotrophic factor in mouse embryonic stem cells. It has been reported that irisin activates AMPK in skeletal muscle DC5 and in neonatal rat cardiomyocytes. The important involvement of irisin in various key metabolic pathways raises interest in its role during human pregnancy. This interest is supported by recent studies showing that circulating levels of irisin increase throughout gestation in pregnant women. The irisin level in maternal circulation was measured to be in the range of 5 to 50 nM in pregnant women during normal gestation, which is significantly higher than the irisin level in nonpregnant women during the luteal phase (approximately 2 nM). The potential contribution of circulating irisin levels to the placenta is currently unknown. Irisin increases throughout gestation, and the trend is significantly altered in pregnancy complications, including gestational diabetes mellitus (GDM), spontaneous preterm birth, and preeclampsia.

Severe preeclampsia (sPE) is a hypertensive disorder affecting 2 to 7% of all pregnancies. It is the leading cause of fetal-maternal morbidity and mortality worldwide. The Preeclampsia Foundation estimated the total short-term health care costs of preeclampsia in 2012, including the usual costs associated with birth, to be $6.4 billion, summed across mothers and infants for all gestational ages in the U.S. Presently, the only available cure is birth. In critical cases, sPE can lead to serious immediate and long-term health complications.

In sPE, reduced uteroplacental perfusion is found, causing placental hypoxia and limited nutrient availability. sPE placentas are characterized by increased inflammatory stress, oxidative damage, and abnormal trophoblast differentiation. The AMPK signaling pathway is intimately involved in the above cellular processes. Additionally, sPE placentas show abnormal protein secretion that contributes to systemic maternal endothelial dysfunction in disease.

Despite ongoing advances in understanding placental development and function, treatments for placental insufficiencies, such as sPE, remain desirable.

SUMMARY

This section provides a general summary of the disclosure, and is not a comprehensive disclosure of its full scope or all of its features.

In various aspects, the current technology provides a method of treating a subject having a placental dysfunction, the method including: administering to the subject a therapeutically effective amount of a composition comprising irisin.

In one aspect, the administering is performed orally, sublingually, intravenously, intramuscularly, intravaginally, subcutaneously, or directly to the placenta of the subject.

In one aspect, the placental dysfunction is preeclampsia, oligohydramnios, intrauterine growth restriction, abnormal placental growth, abnormal angiogenesis, abnormal apoptosis, abnormal oxidative stress, or combinations thereof.

In one aspect, the irisin is recombinant irisin having an amino acid sequence that is at least 80% identical to the amino acid sequence of SEQ ID NO:3, and wherein the recombinant irisin optionally includes a tag.

In one aspect, the irisin is purified from a fluid or a tissue from a human or non-human mammal.

In one aspect, the composition further includes a pharmaceutically acceptable carrier.

In one aspect, the placental dysfunction is preeclampsia and the method further includes administering a therapeutically effective amount of an antihypertensive agent to the subject.

In one aspect, the subject is a human or non-human mammal.

In various aspects, the current technology also provides a method of treating a subject suspected of having a placental dysfunction, the method including obtaining a plurality of cells originating from the subject's placenta or cervix; determining a first irisin level expressed from the plurality of cells; comparing the first irisin level with a second irisin level provided from a normal control; and when the first irisin level is lower than the second irisin level, administering to the subject a therapeutically effective amount of a composition including irisin.

In one aspect, the normal control includes a second plurality of cells originating from a different placenta or cervix of the same subject from a previous pregnancy at a corresponding gestation time.

In one aspect, the normal control includes a second plurality of cells originating from a placenta or cervix of a different subject or plurality of subjects at a corresponding gestation time.

In one aspect, the administering is performed when the first irisin level is at least about 20% lower than the second irisin level.

In one aspect, the administering is performed orally, sublingually, intravenously, intramuscularly, intravaginally, subcutaneously, or directly to the placenta of the subject.

In various aspects, the current technology yet further provides a method of treating a placenta by increasing trophoblast differentiation, increasing placental outgrowth, decreasing trophoblast apoptosis, decreasing oxidative stress, or combinations thereof, the method including contacting the placenta with irisin.

In one aspect, the placenta is in a human or non-human mammalian subject having a placental dysfunction.

In one aspect, the placental dysfunction is oligohydramnios, intrauterine growth restriction, abnormal placental growth, abnormal angiogenesis, abnormal apoptosis, abnormal oxidative stress, or combinations thereof.

In one aspect, the placental dysfunction is preeclampsia.

In one aspect, the contacting the placenta with recombinant irisin results from previously administering a composition comprising the recombinant irisin to the human or non-human mammalian subject.

In one aspect, the administering is performed orally, sublingually, intravenously, intramuscularly, intravaginally, subcutaneously, or directly to the placenta of the subject.

In one aspect, the recombinant irisin is recombinant irisin having an amino acid sequence that is at least 80% identical to the amino acid sequence of SEQ ID NO:3.

In one aspect, the recombinant irisin is delivered to the placenta through an artery.

Further areas of applicability will become apparent from the description provided herein. The description and specific examples in this summary are intended for purposes of illustration only and are not intended to limit the scope of the present disclosure.

DRAWINGS

The patent or application file contains at least one drawing executed in color. Copies of this patent or patent application publication with color drawing(s) will be provided by the Office upon request and payment of the necessary fee.

The drawings described herein are for illustrative purposes only of selected embodiments and not all possible implementations, and are not intended to limit the scope of the present disclosure.

Figure 3:
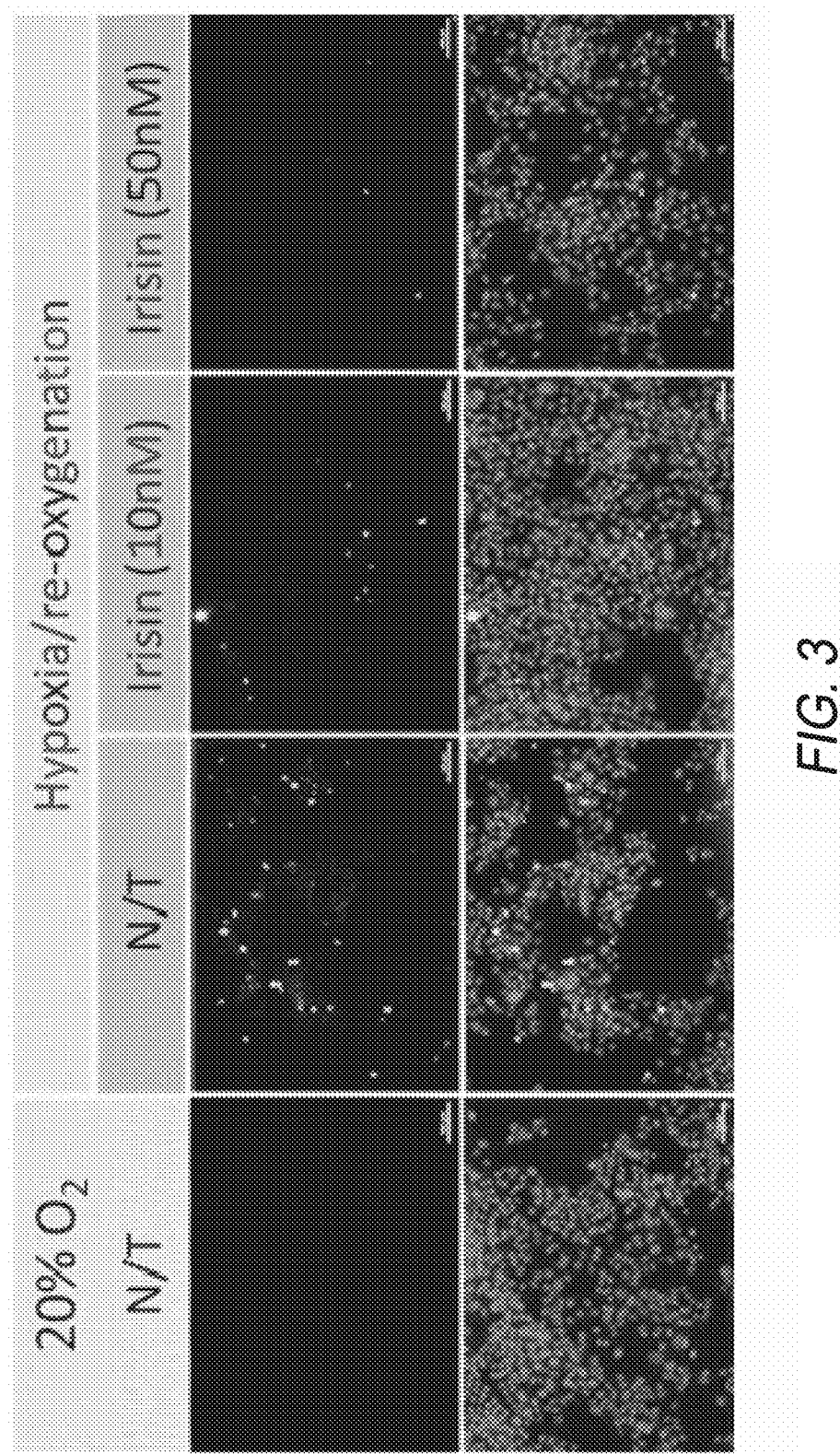

FIG. 3 shows fluorescence micrographs illustrating that irisin decreases hypoxia-induced apoptosis in BeWo trophoblast cells in a dose-dependent manner. In the top panels, apoptotic cells are shown as the. The bottom panels are a merge of the top panels with spotsresulting from nuclear 4,6-diamidino-2-phenylindole hydrochloride (DAPI) staining.

FIGS. 4A-4E show Western blots and corresponding graphs indicating that irisin activates protein kinase B (Akt) (FIG. 4A) and AMPK (FIG. 4B) pathways, reducing pro-apoptotic BAX (FIG. 4C) and BCL2 (FIG. 4D) and inducing cytoprotective HO-1 (FIG. 4E) expression in BeWo Cells.

Figure 5A:
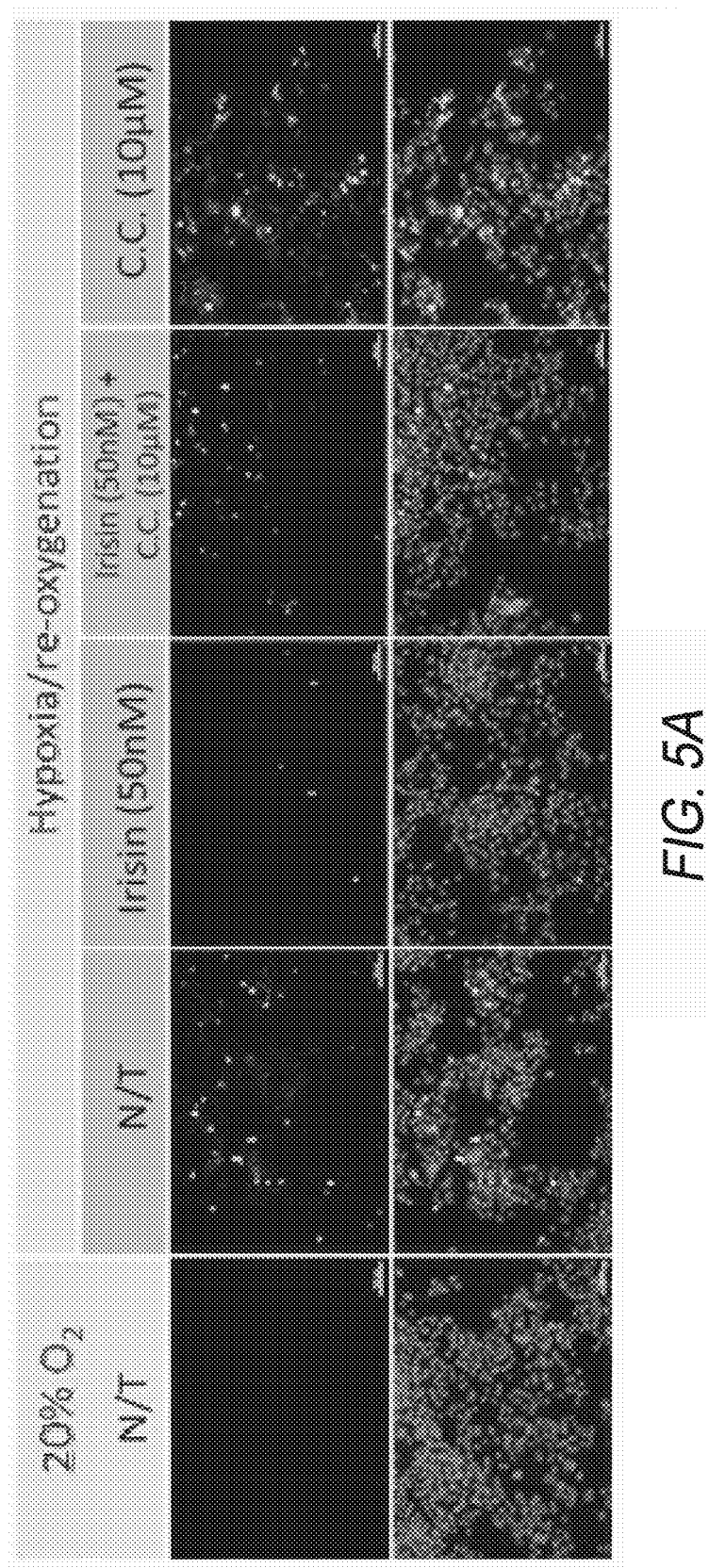
Figure 5B:
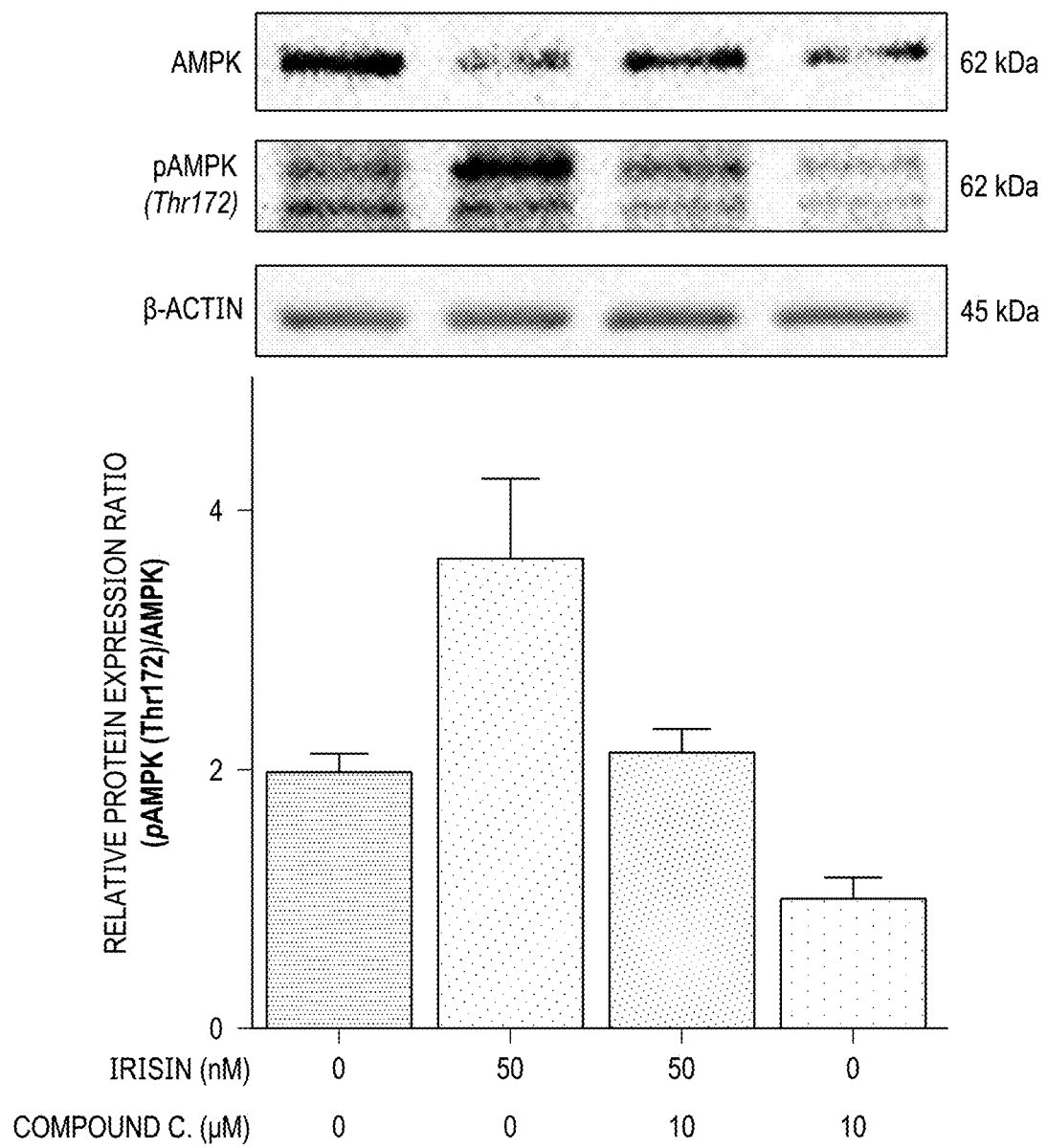

FIGS. 5A-5B show that the effects of irisin on apoptosis are mediated via AMPK and blocked by compound C in hypoxia-treated BeWo cells. FIG. 5A shows fluorescence micrographs. In the top panels, apoptotic cells are shown as the spots. The bottom panels are a merge of the top panels with spots resulting from nuclear DAPI staining. FIG. 5B shows Western blots and a corresponding bar graph demonstrating that the effects of irisin on apoptosis are mediated via AMPK and blocked by compound C in hypoxia-treated BeWo cells.

Figure 6A:
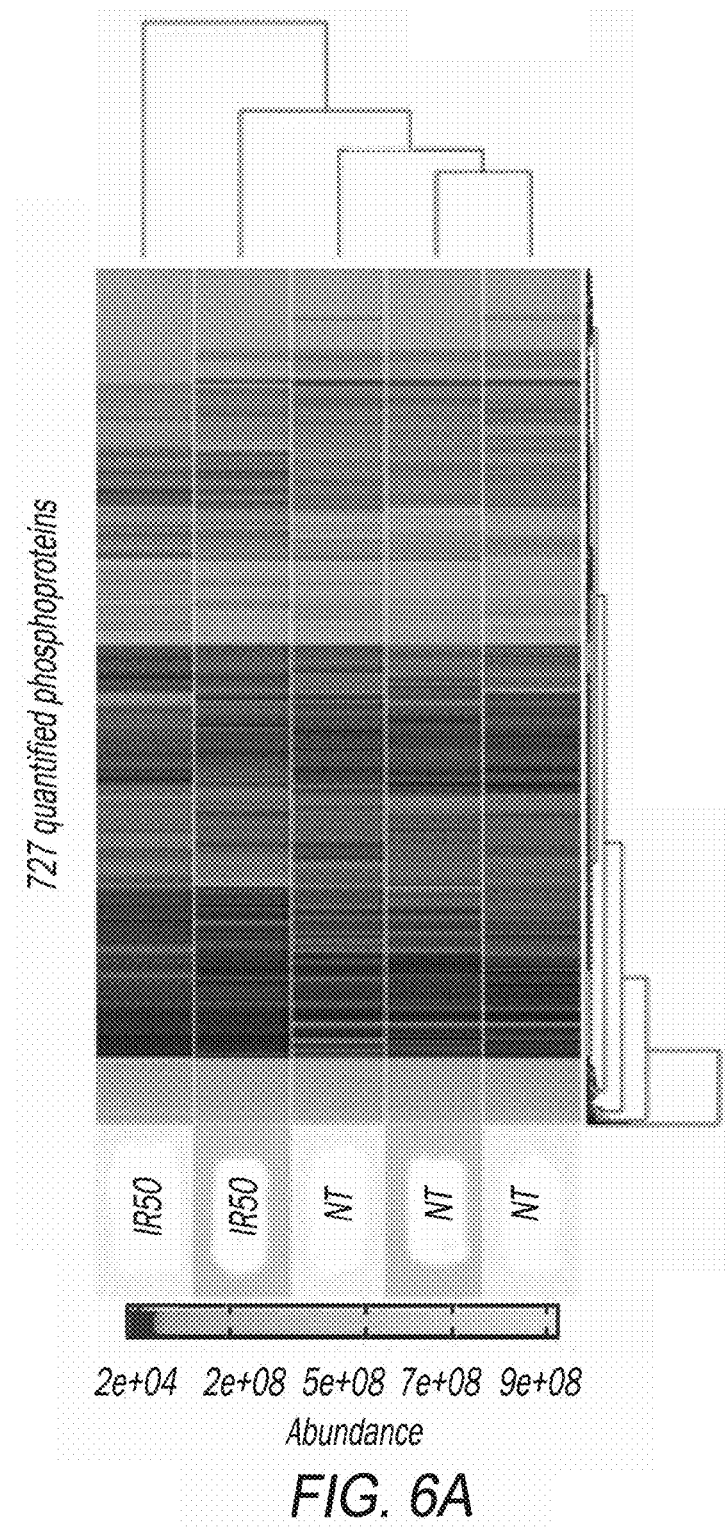
Figure 6B:
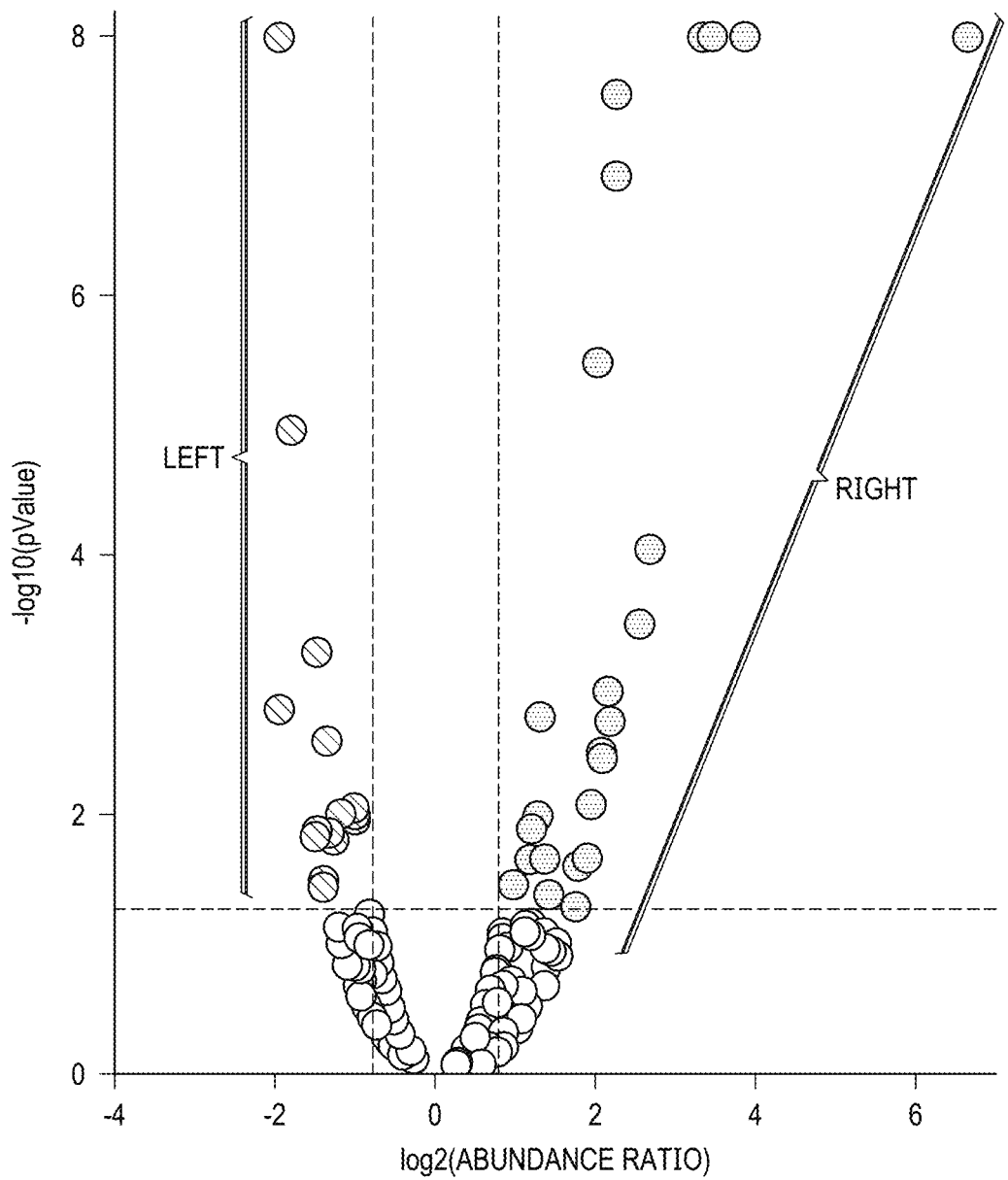
Figures 6C, 6D:
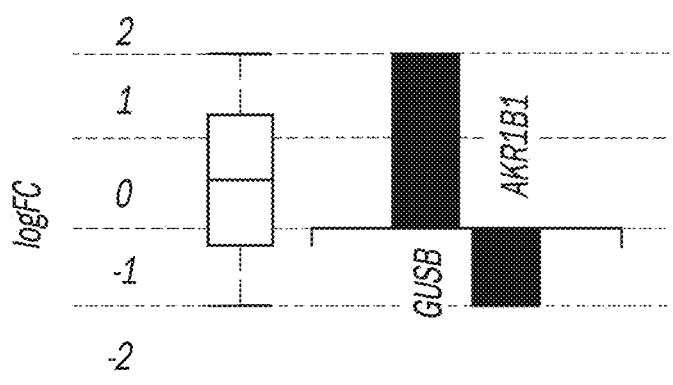
Figure 6E:
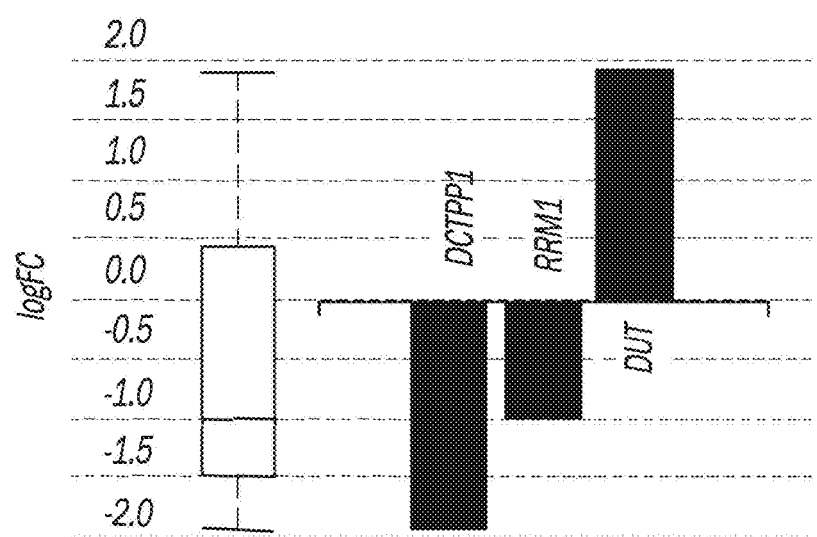

FIGS. 6A-6E show a phosphoproteomic profile of irisin-treated (50 nM for 1 hour; n=2) BeWo cells versus untreated controls (n=3). FIG. 6A shows a heat map of a hierarchical clustering of samples showing a distinct abundance pattern of phosphopeptides in irisin-treated cells. FIG. 6B is a volcano plot depicting a change of phosphopeptides. All abundance ratios (fold changes) are log 2 transformed (x-axis) and plotted against the −log 10 transformed statistical significance (y-axis). From 727 curated phosphopeptides, those with at least a two-fold increase (right; n=31) or decrease (left; n=16) by exposure to irisin with $p<0.05$ are indicated. FIG. 6C shows a functional analysis of irisin-induced phosphoproteome changes performed on an iPathwayGuide/Advaita platform with the top five terms enriched in "Biological Pathways" identified. It is revealed that irisin significantly alters the abundances of phosphopeptides that belong to two metabolic pathways—"pyrimidine metabolism" (as shown in FIG. 6D) and "pentose and glucuronate interconversions" (as shown in FIG. 6E).

Figure 7A:
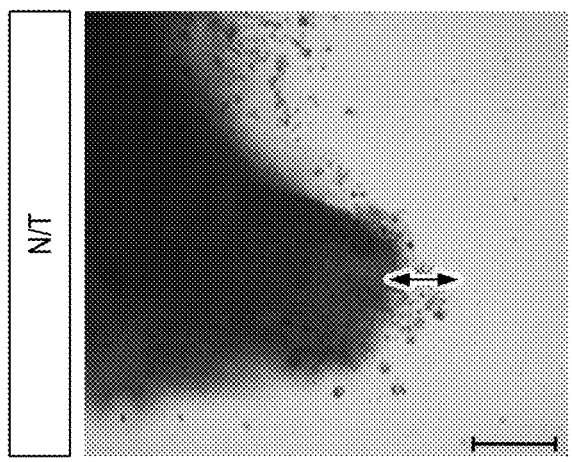
Figure 7B:
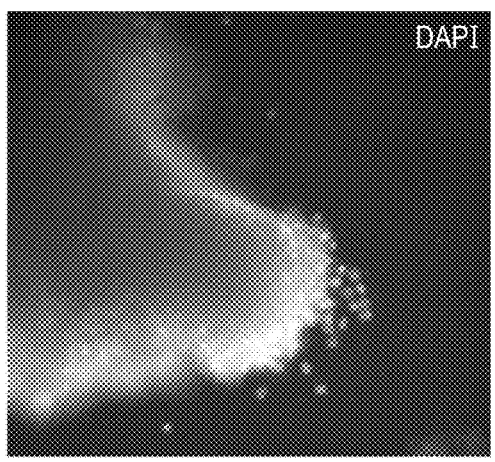
Figure 7C:
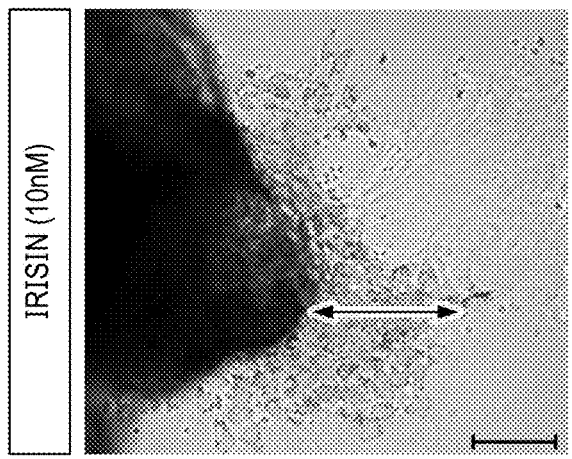
Figure 7D:
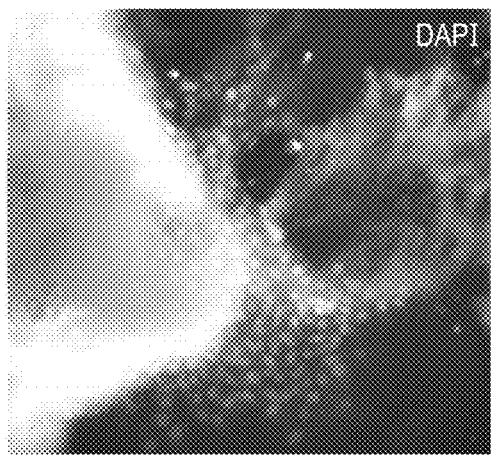
Figure 7E:
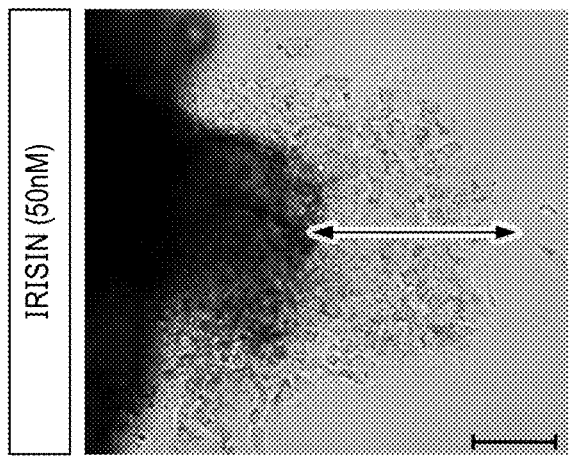
Figure 7F:
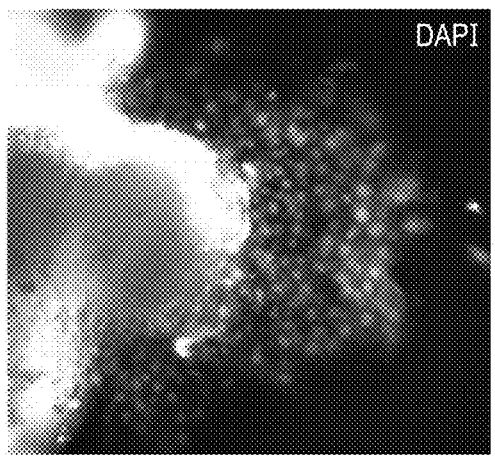
Figure 7H:
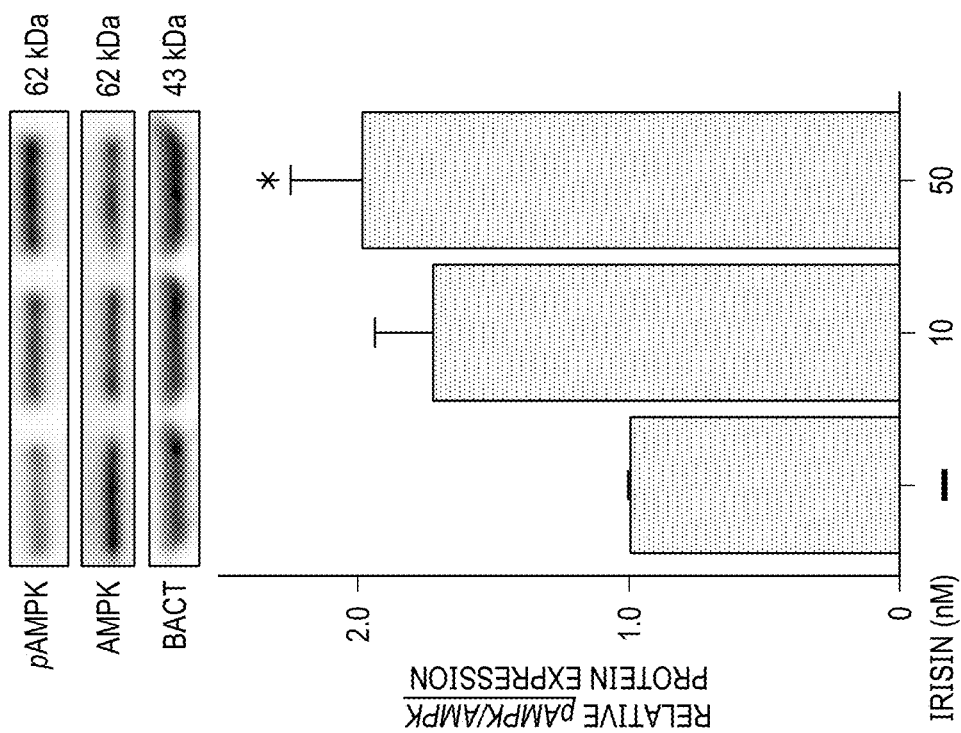
Figure 7G:
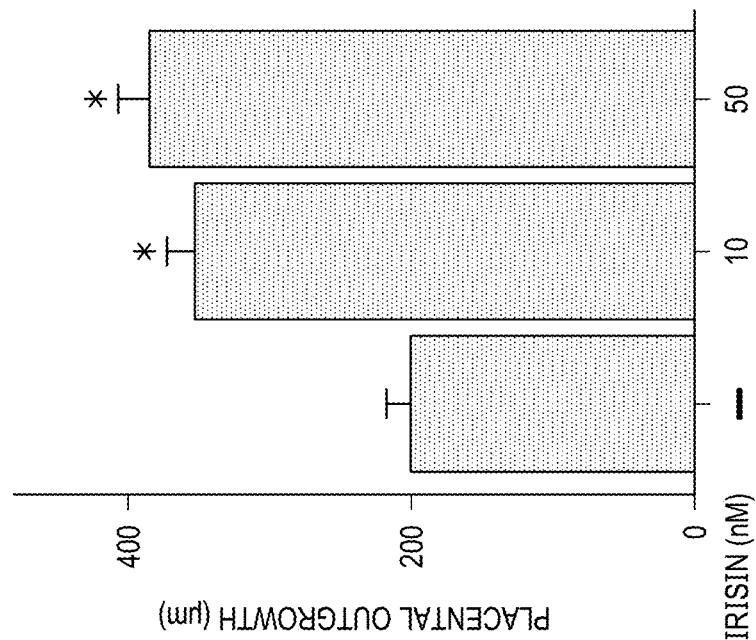

FIGS. 7A-7H show that irisin promotes EVT differentiation and trophoblast invasion in first-trimester placental explants. After an overnight culture on Matrigel®-coated Transwell® inserts, first-trimester villi were treated with 0 nM (nontreatment (NT) control), 10 nM, or 50 nM irisin for 48 hours before fixation. FIGS. 7A, 7C, and 7E are representative bright-field images showing outgrowths from villous explants (scale bar=200 µm), and FIGS. 7B, 7D, and 7F are corresponding images showing DAPI-labeled nuclei. FIG. 7G is a bar plot showing outgrowth lengths for triplicate experiments in which ten villous explants were measured for each treatment. FIG. 7H provides Western blots and a corresponding bar graph showing that epithelial marker E-cadherin (CDH1) was remarkably reduced by exposure to irisin. In FIGS. 7A-7H, n=5, *$p<0.05$ versus NT controls, and bars represent mean±standard error of the mean.

Figure 8A:
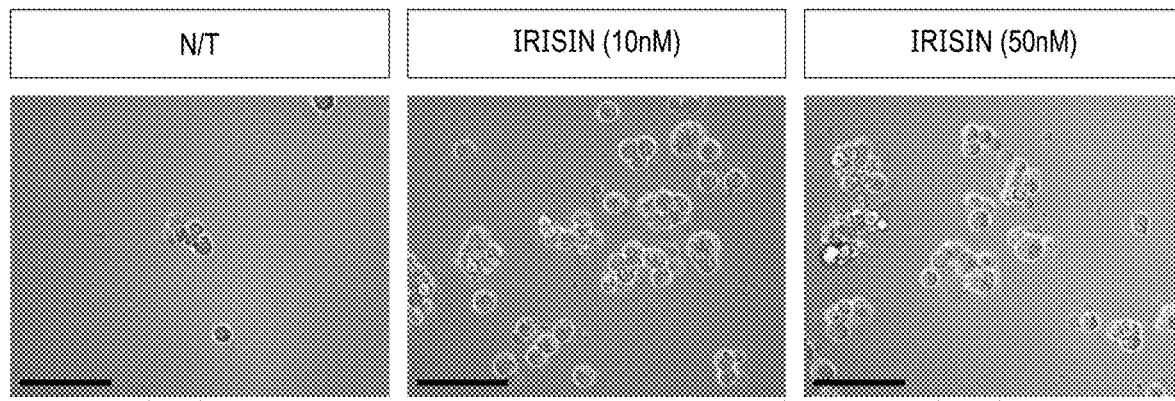
Figure 8B:
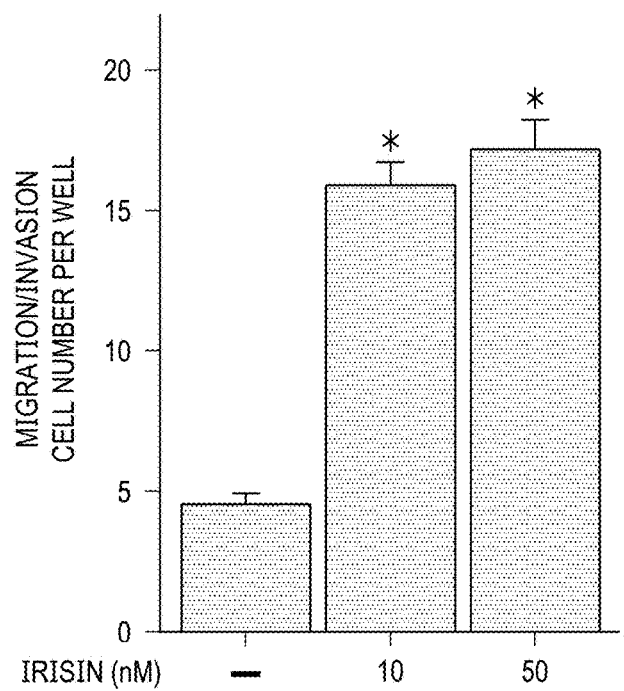
Figure 8C:
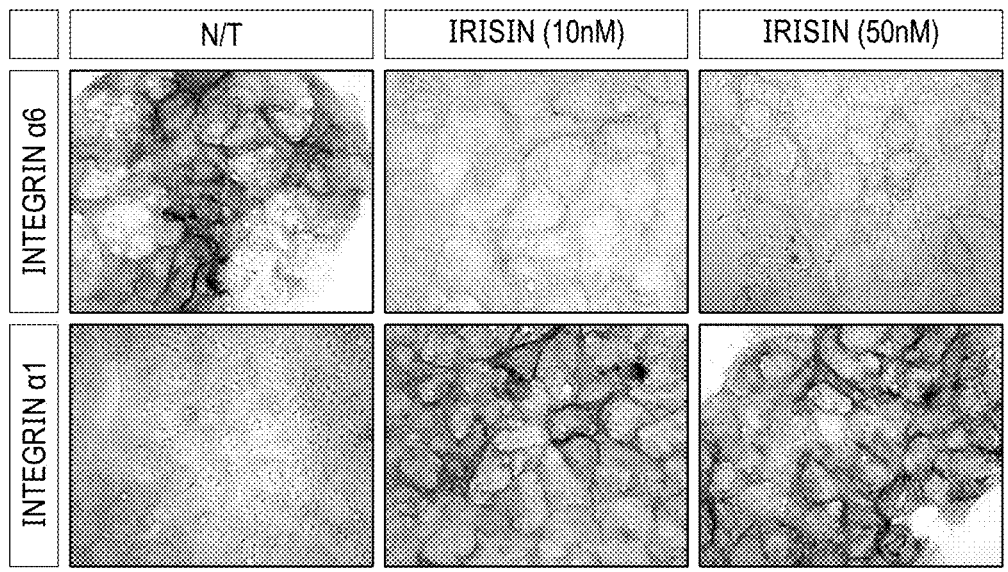
Figure 8D:
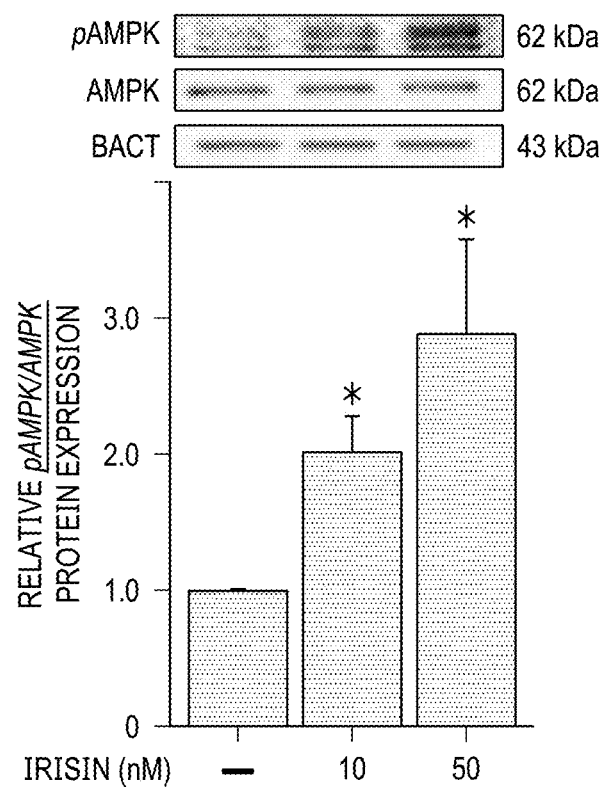

FIGS. 8A-8D show that irisin induces invasion in trophoblast cells in vitro. The invasive capacity of HTR-8/SVneo cells increased after being cultured for 72 hours in the presence of irisin on Matrigel®-coated Transwell® inserts. FIG. 8A shows bright-field micrographs of exemplary cells that penetrated through the Matrigel® after culture with (10 and 50 nM) or without (N/T) different concentrations of irisin (scale bars=100 µm). Cells that invaded through the Matrigel® were trypsinized from the bottom of the insert, fixed, and counted, with the data presented as a bar chart in FIG. 8B. Irisin treatment also promoted the expression of a proinvasive integrin subunit ($\alpha 1$) and decreased a proliferative/anti-invasive integrin subunit ($\alpha 6$), as confirmed by immunohistochemistry in FIG. 8C. FIG. 8D provides Western blots and a corresponding bar graph showing that increased invasion and migration in HTR-8/SVneo cells is accompanied by AMPK activations. In FIGS. 8A-8D, n=3; *$p<0.05$ versus NT controls, and bars represent mean±standard error of the mean.

Figure 9A:
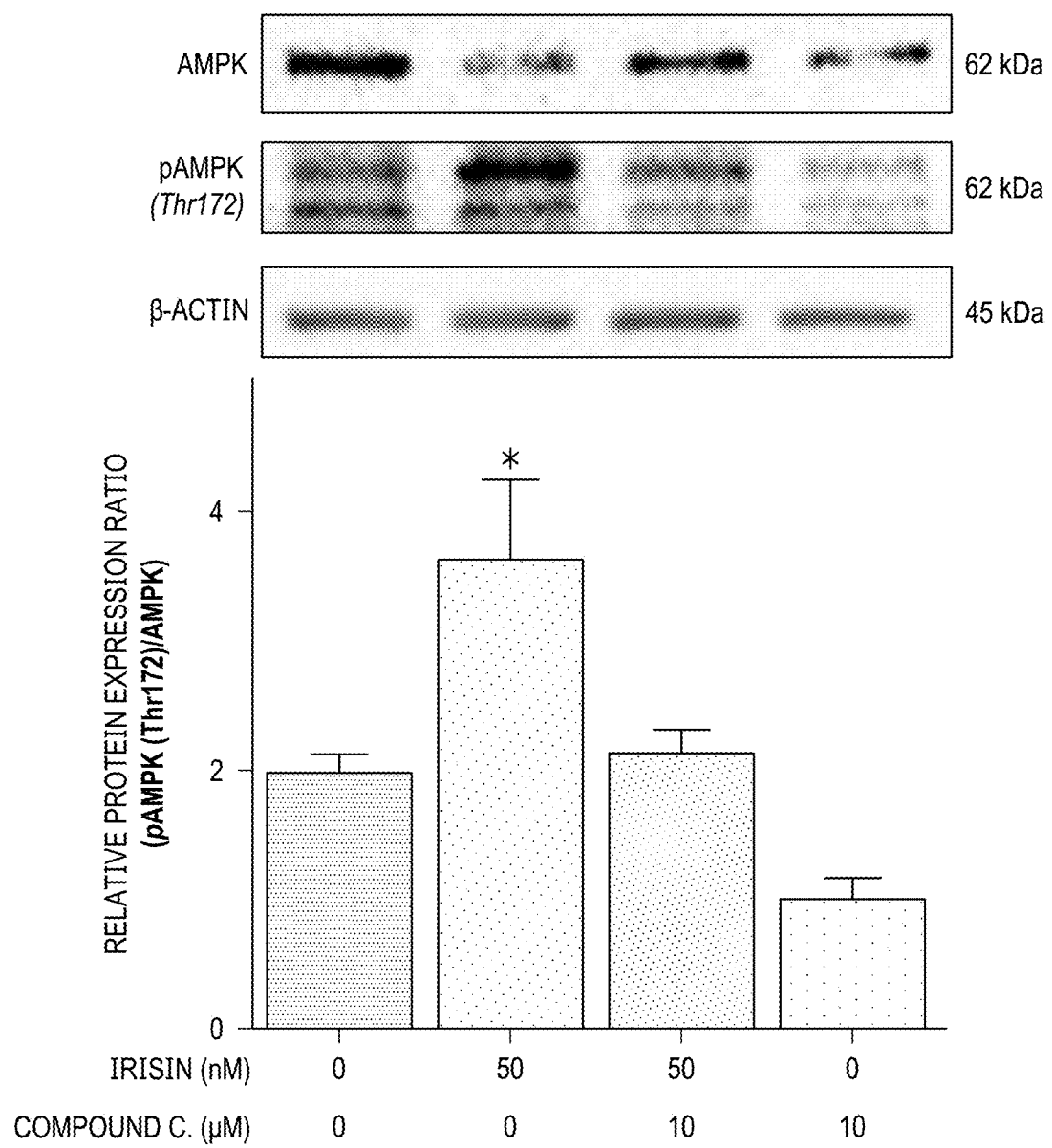
Figure 9B:
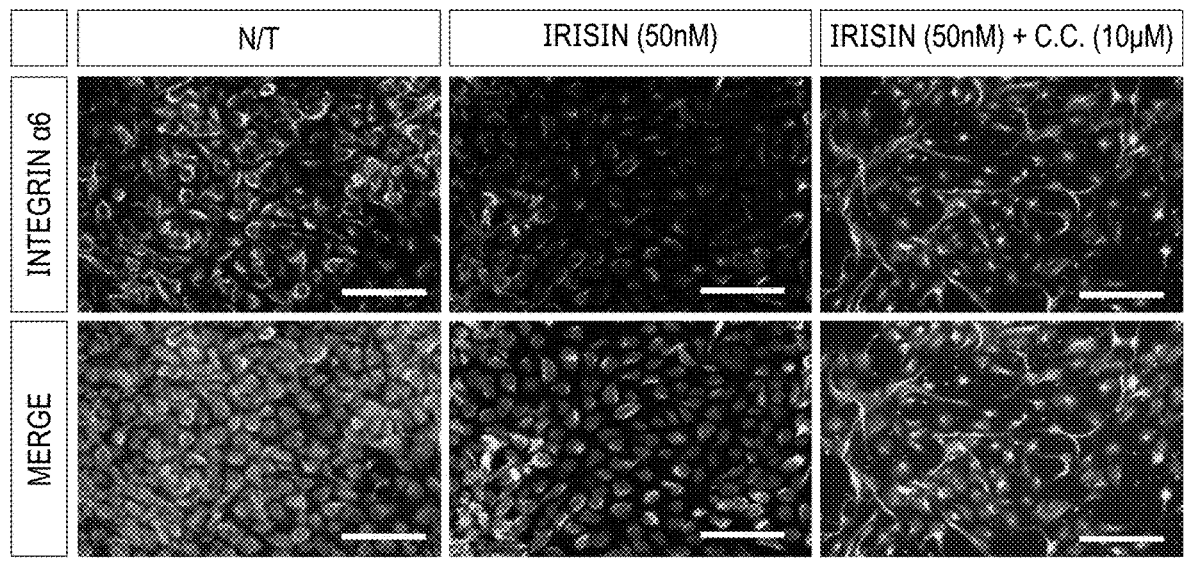
Figure 9C:
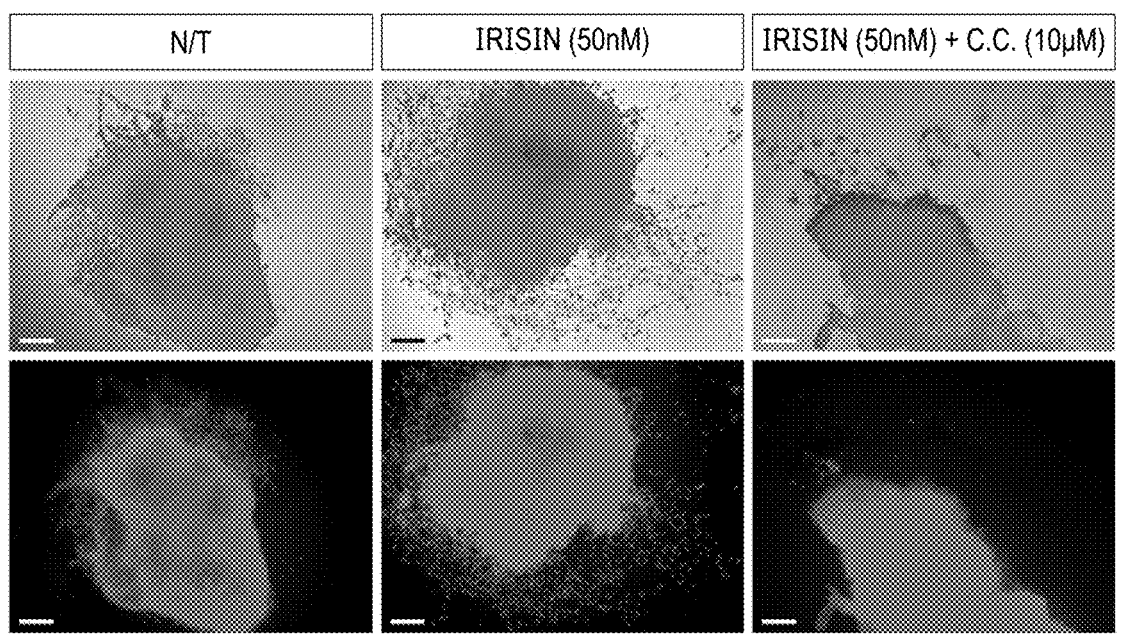

FIGS. 9A-9C show that antagonizing AMPK inhibits irisin-induced differentiation and invasion in trophoblast cells. HTR-8/SVneo cells were incubated in the presence of nothing (nontreatment (NT) control), irisin, irisin after pretreatment with compound C, and only compound C for 24 hours. FIG. 9A provides Western blots and a corresponding bar graph showing that pretreatment (2 hours) with 10 µM compound C reverts the positive effect of irisin on AMPK activation. FIG. 9B provides immunohistochemistry fluorescence micrographs showing that the negative effect of irisin on the intracellular expression of an anti-invasive integrin subunit ($\alpha 6$) was also antagonized in the presence of 10 µM compound C (scale bars=100 µm). Similarly, FIG. 9C provides micrographs showing that 50 nM irisin induces trophoblast differentiation and migration, which were blocked in the first-trimester placenta by exposure to 10 µM compound C (scale bars=100 µm). In FIGS. 9A-9C, *$p<0.05$ versus NT controls, and bars represent mean±standard error of the mean.

Figure 10C:
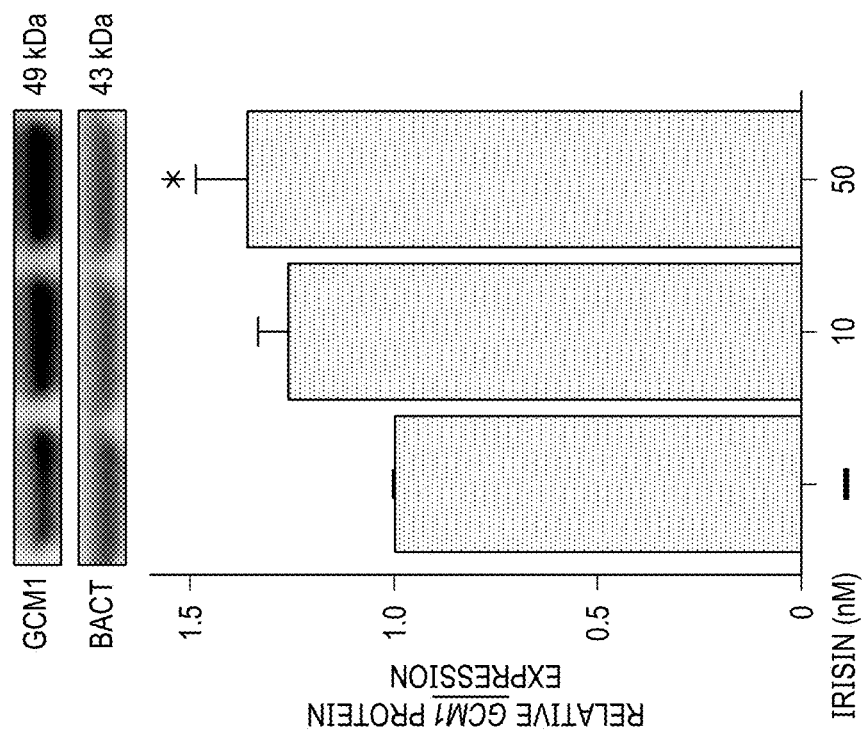
Figure 10A:
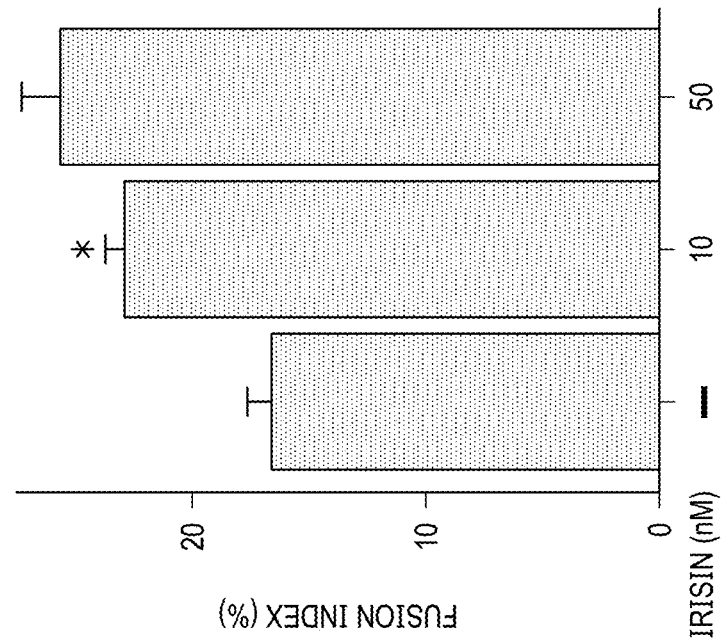
Figure 10B:
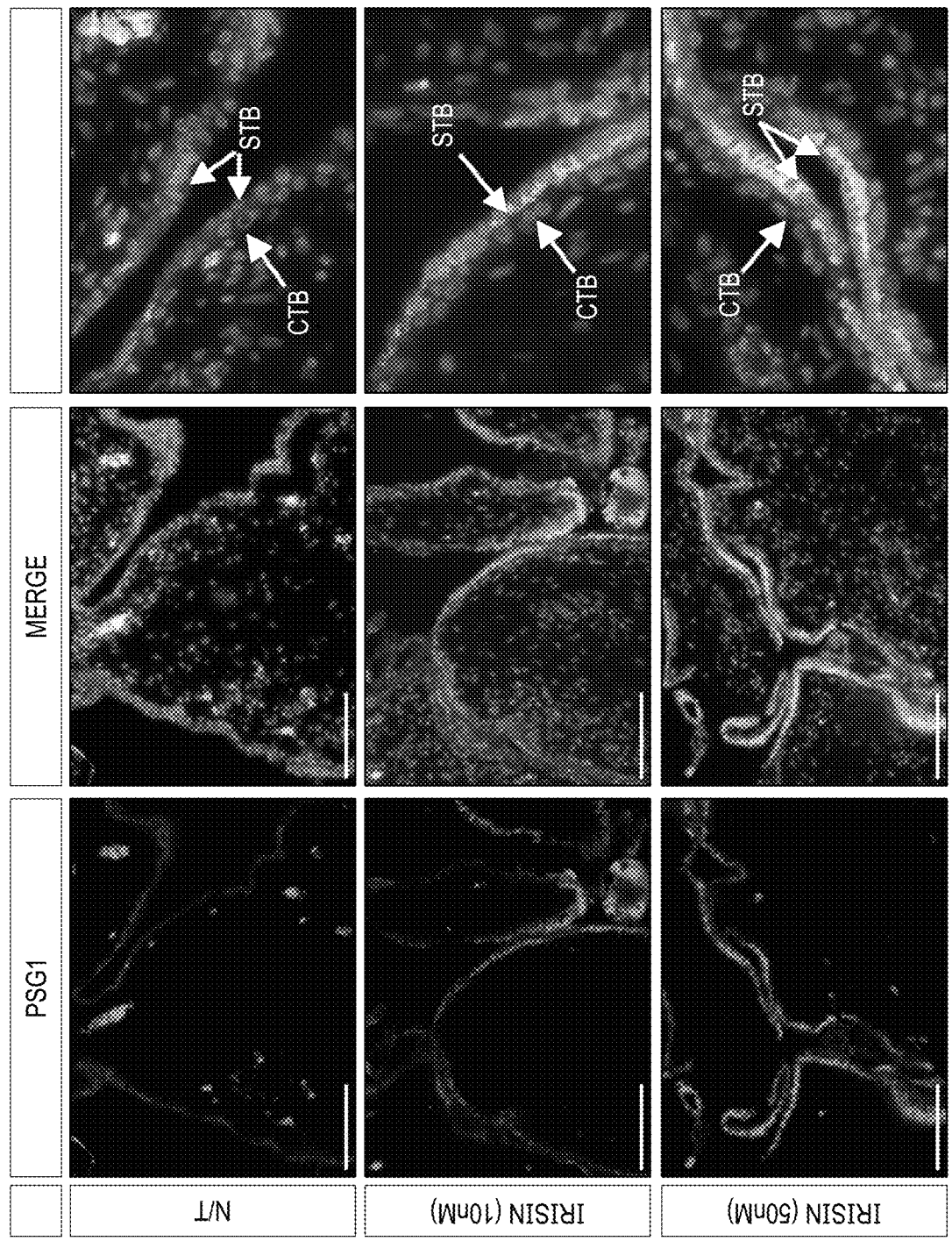

FIGS. 10A-10C show that irisin induces STB formation in first-trimester trophoblast cells. FIG. 10A is a bar graph showing that irisin treatment significantly increases the fusion index in first-trimester placenta explants, as determined by the percentage of nuclei numbers in syncytia. FIG. 10B provides fluorescence micrographs showing that the elevations in placental trophoblast fusion and differentiation, versus a nontreatment (NT) control, are accompanied by significant increases in protein expression of the STB differentiation marker pregnancy-specific β-1-glycoprotein 1 (PSG1; scale bars=100 µm). FIG. 10C provides Western blots and a corresponding bar graph showing that the elevations in placental trophoblast fusion and differentiation are also accompanied by significant increases in protein expression of the STB differentiation marker GCM1. In FIGS. 10A-10C, n=5; *$p<0.05$ versus NT controls, and bars represent mean±standard error of the mean.

Figure 11A:
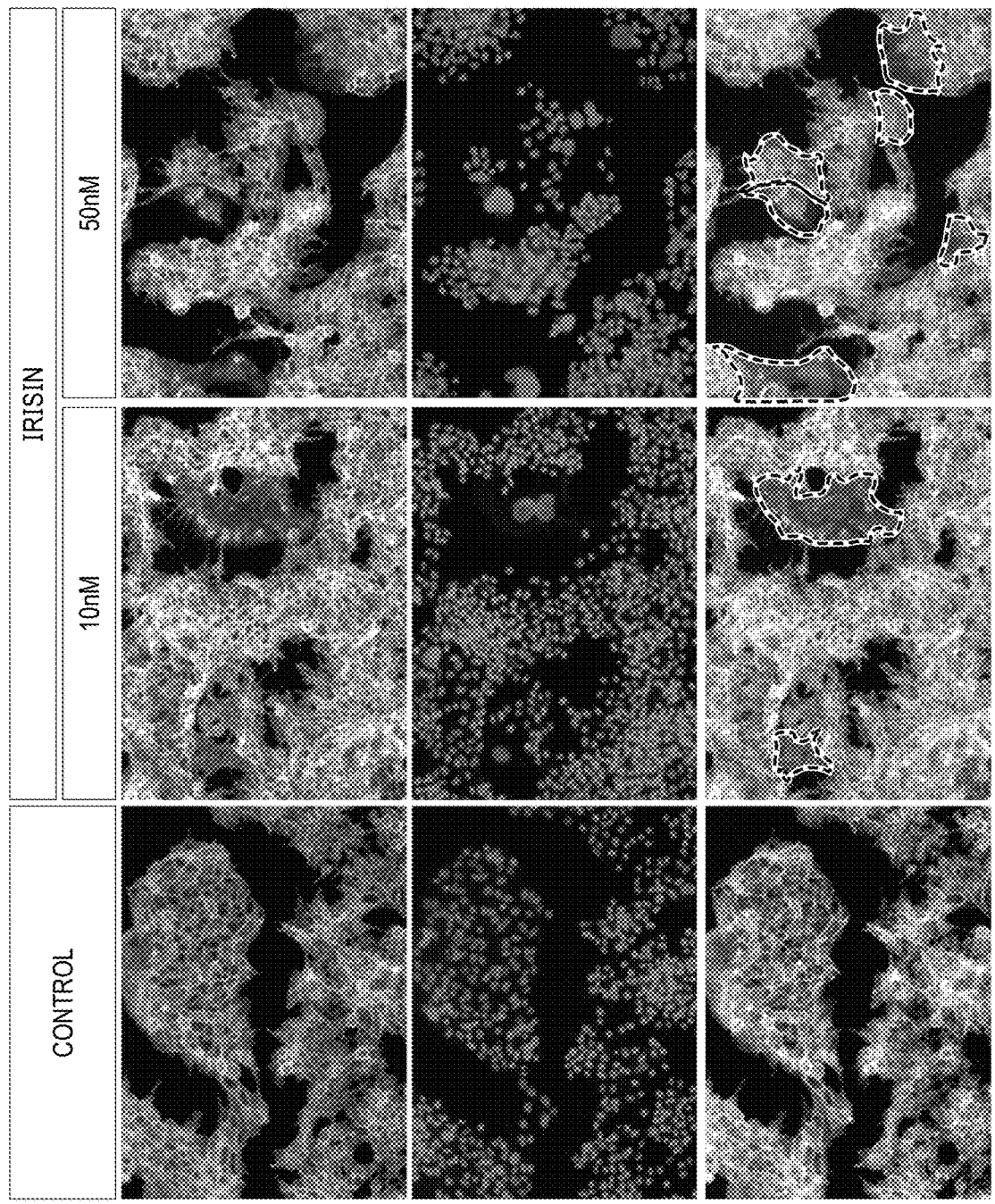
Figure 11C:
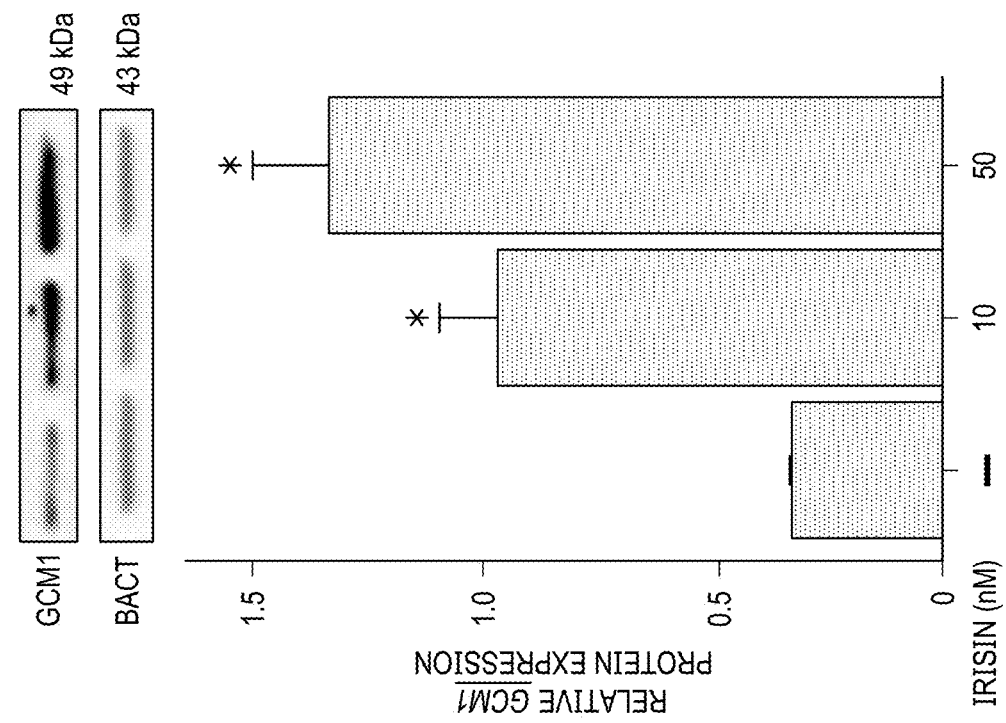
Figure 11B:
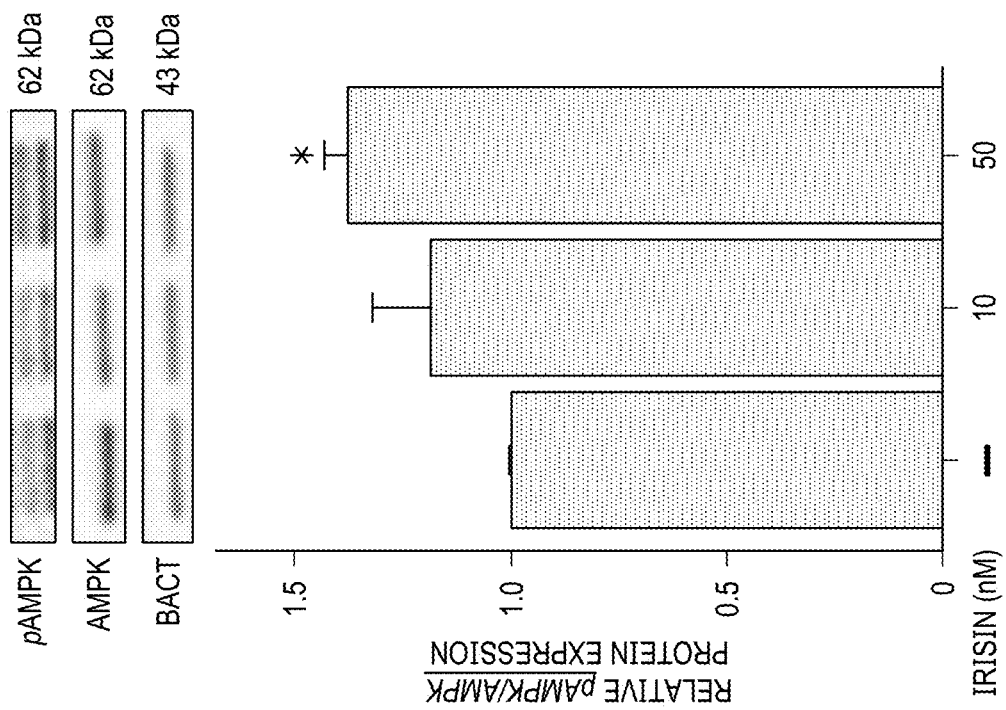
Figure 11D:
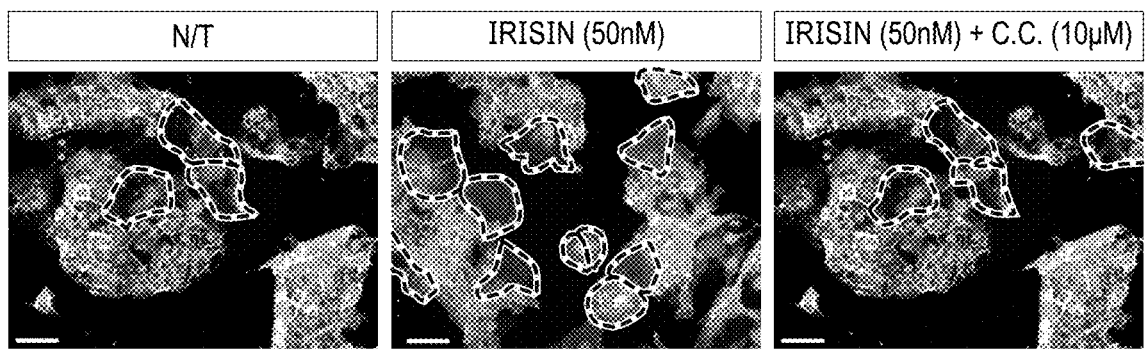
Figure 11E:
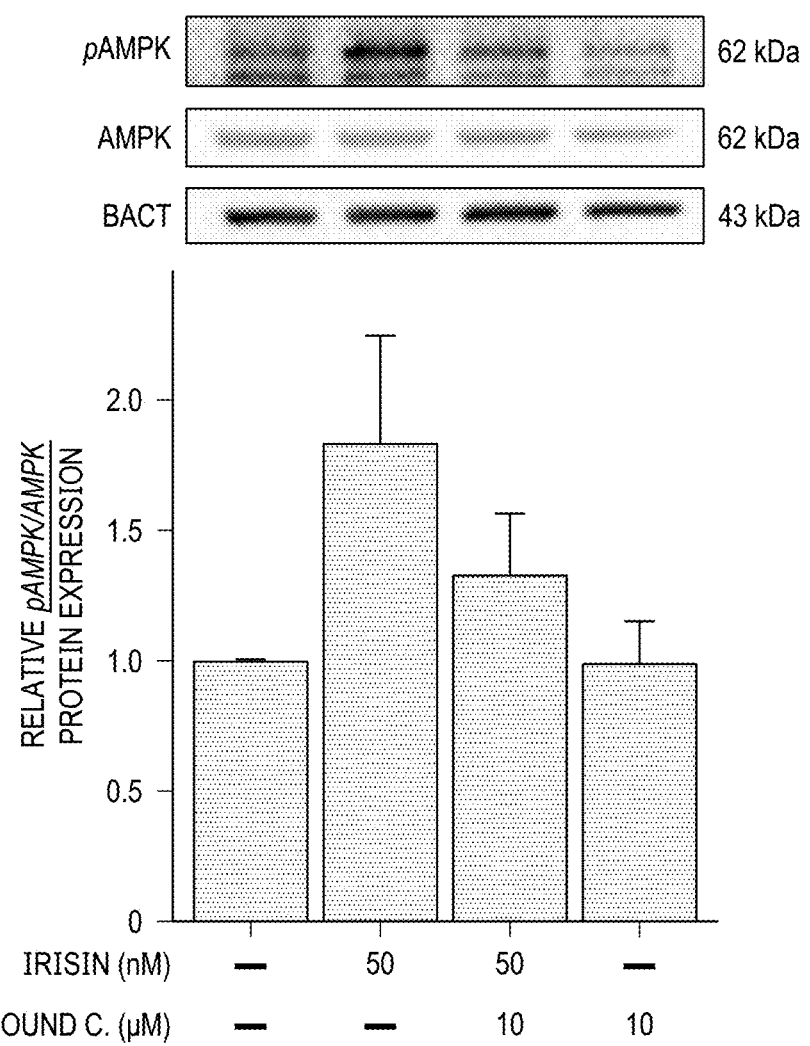

FIGS. 11A-11E show that CTB differentiation and syncytialization are promoted by irisin in vitro and can be blocked in the presence of an AMPK antagonist. The CTB-like cells of the human choriocarcinoma (BeWo) were exposed to nothing (nontreatment (NT) control) or increasing concentrations (10 and 50 nM) of irisin for 72 hours. Cells undergo fusion and morphological differentiation after treatment with irisin. An E-cadherin antibody was used to stain the cell wall. FIG. 11A provides fluorescence micrographs showing that syncytium formation (large multinuclei cytoplasmic masses; indicated by dashed lines) is increased in the presence of irisin in a dose-dependent manner. FIGS. 11B-11C provide Western blots with corresponding bar graphs showing that this event is accompanied by an increase in the expression of phosphorylated AMPK (pAMPK) and GCM1, respectively. FIG. 11D provides fluorescence micrographs showing that pretreatment (2 hours) with 10 µM compound C blocks irisin-induced (50 nM) STB formation (syncytia are marked by dashed lines; scale bars=100 µm), and FIG. 11E provides Western blots and a corresponding bar graph showing that the compound C pretreatment also blocks AMPK activation. In FIGS. 11A-11E, *$p<0.05$ versus NT controls, and bars represent mean±standard error of the mean.

Figure 12:
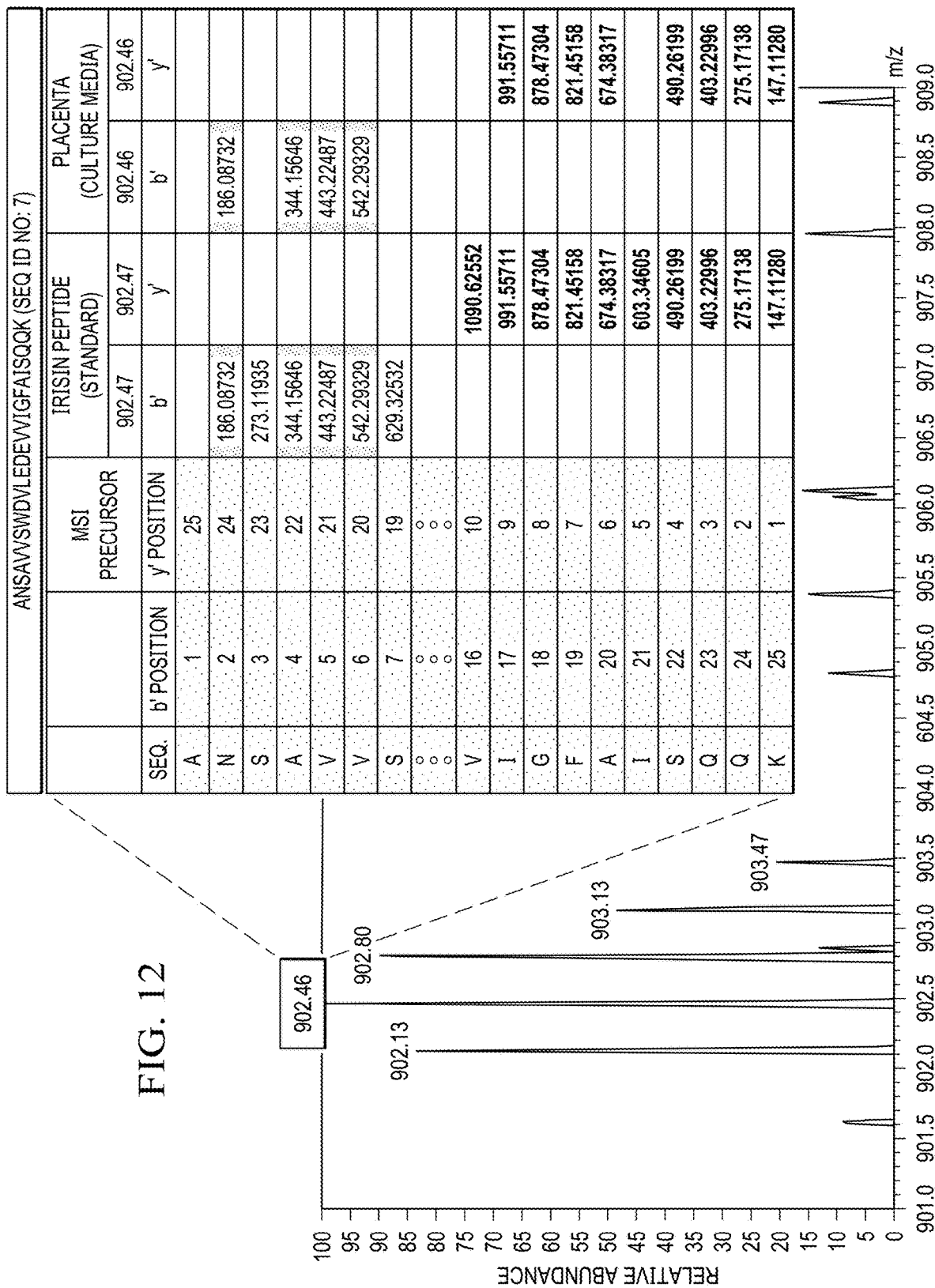

FIG. 12 shows the detection of secreted irisin peptide in term placenta culture media by mass spectrometry (MS). Placental explants were cultured for 24 hours. The recombinant irisin peptide (Enzo Life Science; ADI-908-307) served as control. Culture media were trypsinized and subjected to LC-MS/MS analysis. The most abundant precursor (identical between standard and culture media) at MS1 (m/z=902.46) was further analyzed by MS2. b+ and y+ MS2 fragment ions were used to identify the target peptide from standard solution and the placenta culture media. Twelve of the sixteen fragments found in standard solution were also identified in the culture media. Four b+ fragment ions in culture media were identical to those in standard irisin. A unique 25aa long peptide that matched to irisin peptide (aa47-aa72 of full length FNDC5) was identified, revealing the presence of secreted irisin from human placental explant.

Retention times for each peptide are labeled on the x-axis. The y-axis represents relative intensity for each y-ion peak.

Figure 13A:
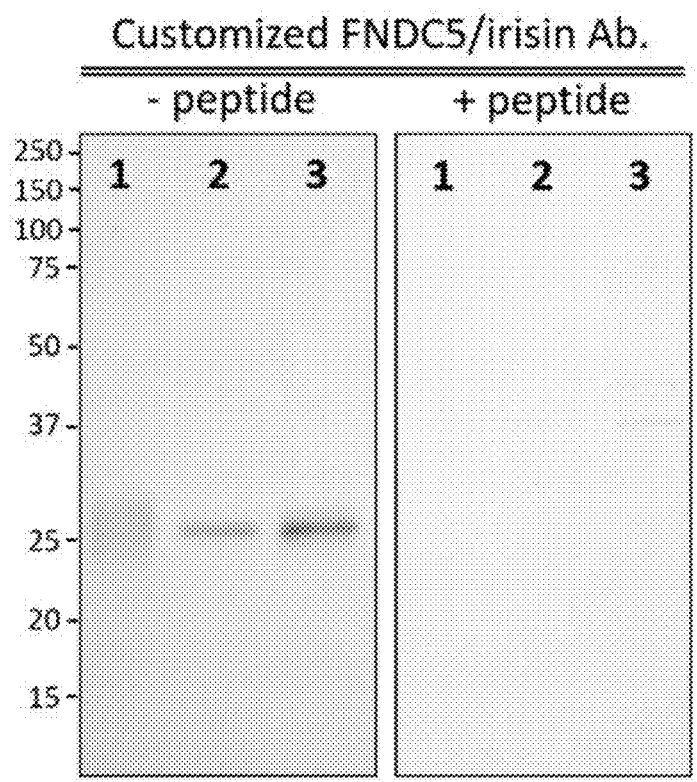
Figure 13B:
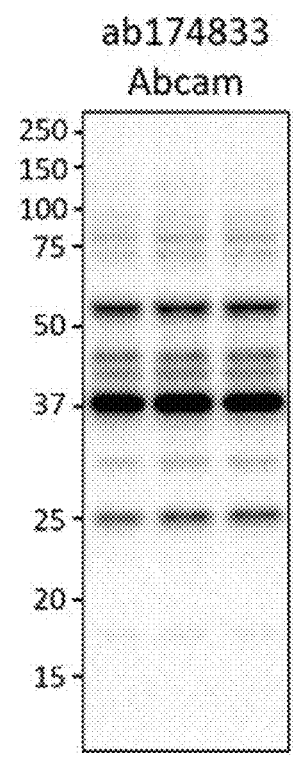

FIGS. 13A-13B show that custom polyclonal antibody (Ab) detects FNDC5/irisin with high specificity. The custom polyclonal Ab was designed against the fibronectin III domain (irisin) region of FNDC5 protein. As shown in FIG. 13A, immunoblotting of trophoblast cell line extracts with this Ab detect a single band at 24 kDa. The specificity of the FNDC5/irisin Ab was verified by an immunizing peptide blocking experiment. Pre-incubation of antibody with FNDC5 peptide blocked the signal. Lane 1 is the recombinant irisin peptide (Enzo Life Science; ADI-908-307), which served as a control; lane 2 is BeWo trophoblast cell line protein extract; and lane 3 is HTR-8/SVneo trophoblast cell extract. FIG. 13B shows that in another experiment, three replicates of BeWo trophoblast cells extract were immunoblotted with a commercial FNDC5 antibody (ab174833; Abcam). Multiple bands raise doubts about the specificity of the commercial antibody and further support the superior specificity of the custom Ab.

Figure 14A:
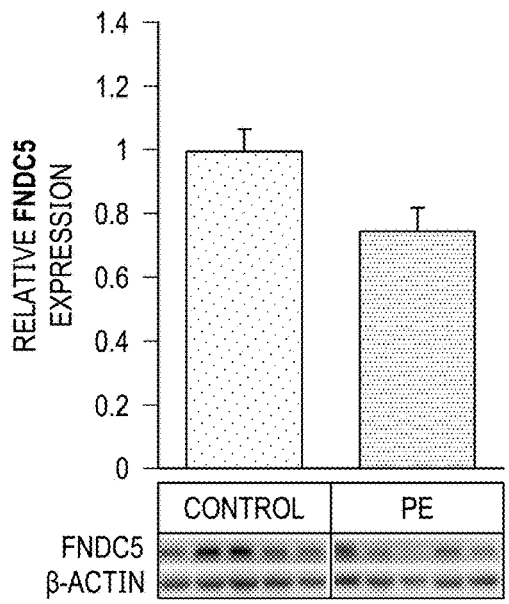
Figure 14B:
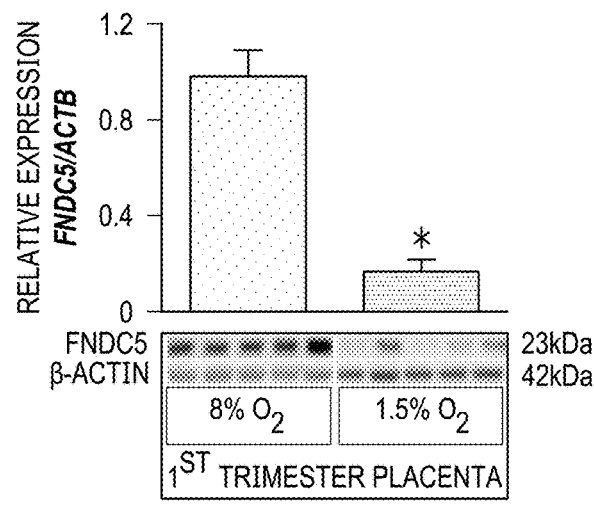
Figure 14C:
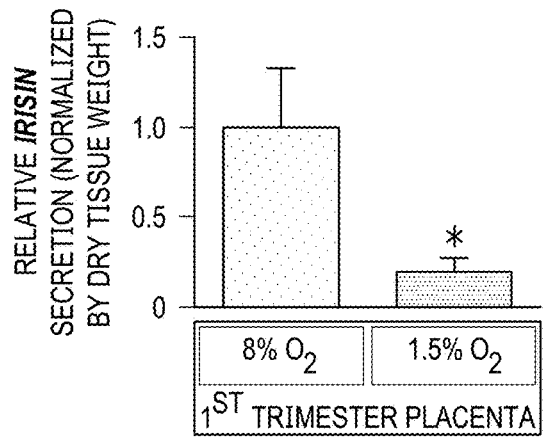

FIGS. 14A-14C show that irisin is expressed from the placenta. FIG. 14A provides Western blots and a corresponding bar graph showing intracellular expression of FNDC5 in healthy and preeclampsia term placenta. FIG. 14B provides Western blots and a corresponding bar graph showing intracellular expression of FNDC5 in first-trimester placental explants incubated overnight in hypoxia (1.5% O2). FIG. 14C shows that irisin secretion into culture media is also reduced under hypoxic condition. In FIGS. 14A-14C, n=5 and *p<0.05.

Figure 15:
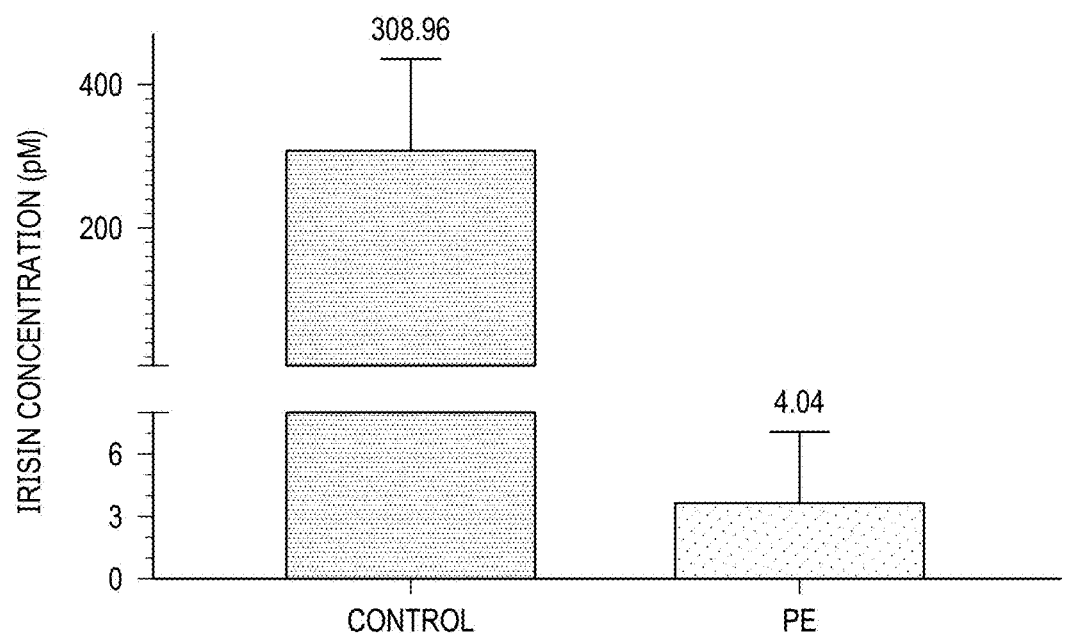

FIG. 15 is a bar graph showing that irisin secretion from the placenta is dramatically lower in preeclampsia pregnancies. Term placenta explants obtained from preeclampsia (n=2) and age-matched controls (n=3) were incubated overnight in culture media. Irisin concentration was measured by mass spectrometry (see FIG. 12). Concentrations are normalized by tissue weights and shown as mean±standard error of the mean.

Figure 16:
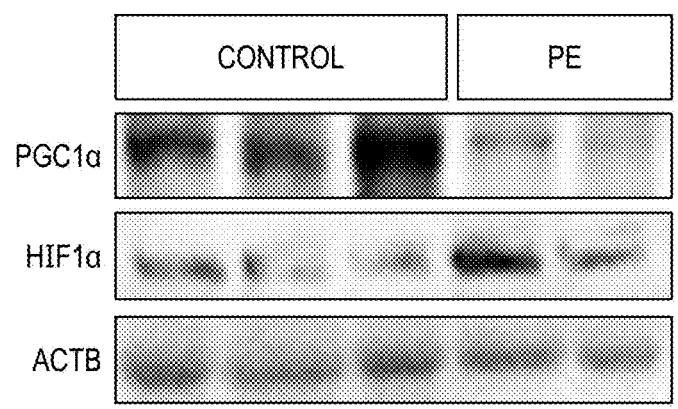

FIG. 16 provides Western blots showing that PGC1a down-regulation coincides with HIF1a upregulation in preeclampsia placentas compared to healthy controls. Term placentas obtained from preeclampsia (n=2) and age-matched controls (n=3) were detected by Western blot using antibodies against PGC1a and HIF1α. Beta-actin (ACTB) served as internal control.

Figure 17:
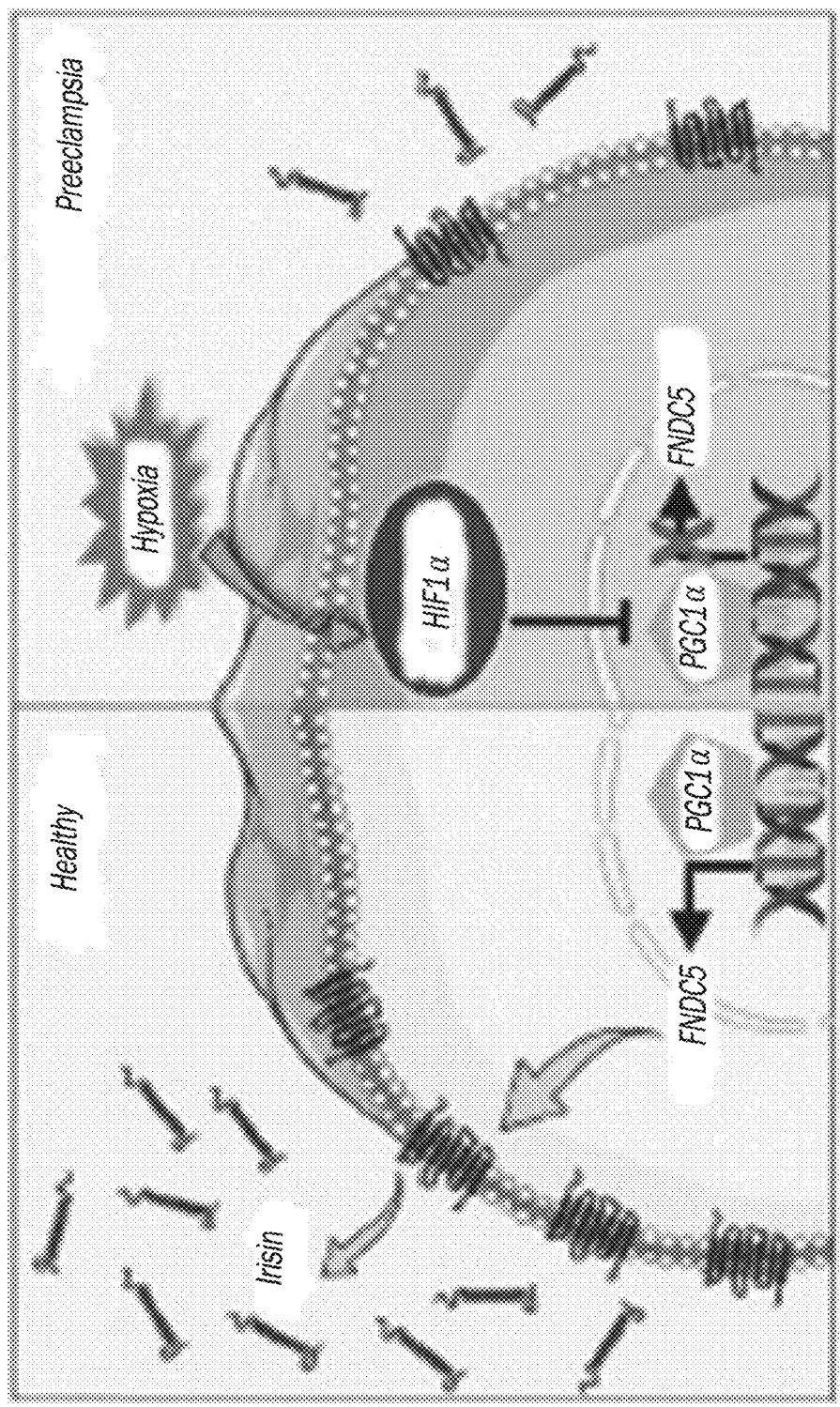

FIG. 17 is an illustration showing PGC1a modulating FNDC5 expression. It is believed that in a preeclampsia placenta, PGC1a is suppressed by overexpressed HIF1α that negatively impacts FNDC5 expression and subsequently irisin secretion from trophoblasts.

Figures 18A, 18B, 18C:
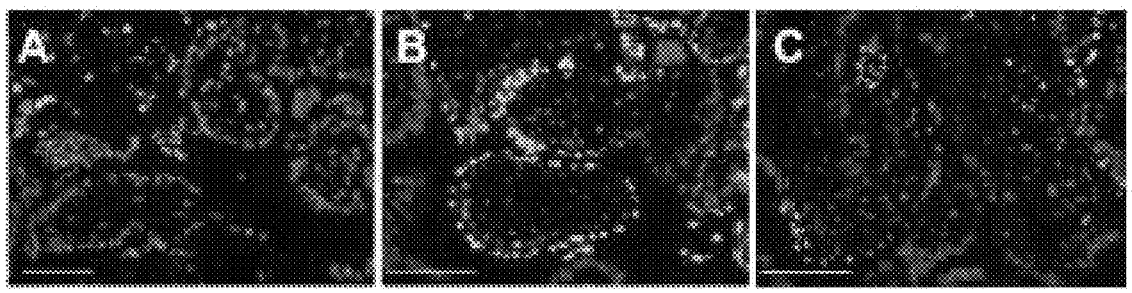

FIGS. 18A-18C are fluorescent micrographs showing that irisin prevents hypoxia-induced apoptosis in placental explants. First-trimester placenta explants were incubated under normoxia (8% O2; FIG. 18A), hypoxia (1.5% O2; FIG. 18C), or without exposure to 50 nM irisin (FIG. 18B). Apoptotic cells were visualized (light green) by TUNEL assay. The scale bars are 50 μm.

Figure 19A:
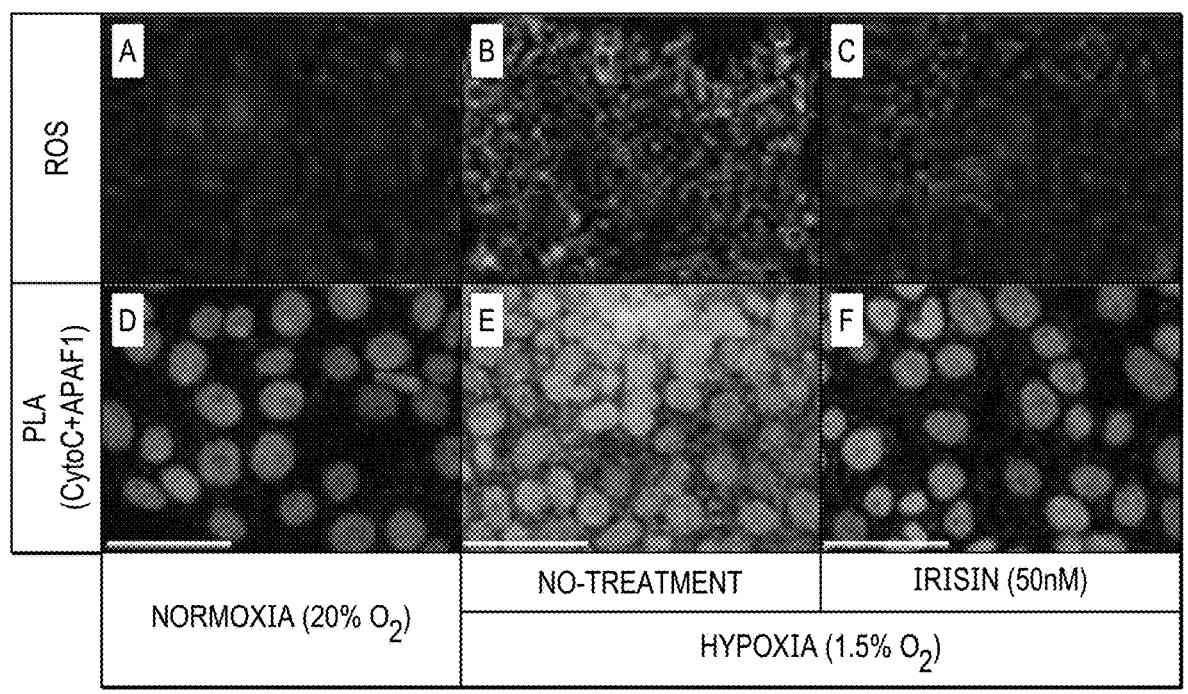
Figure 19B:
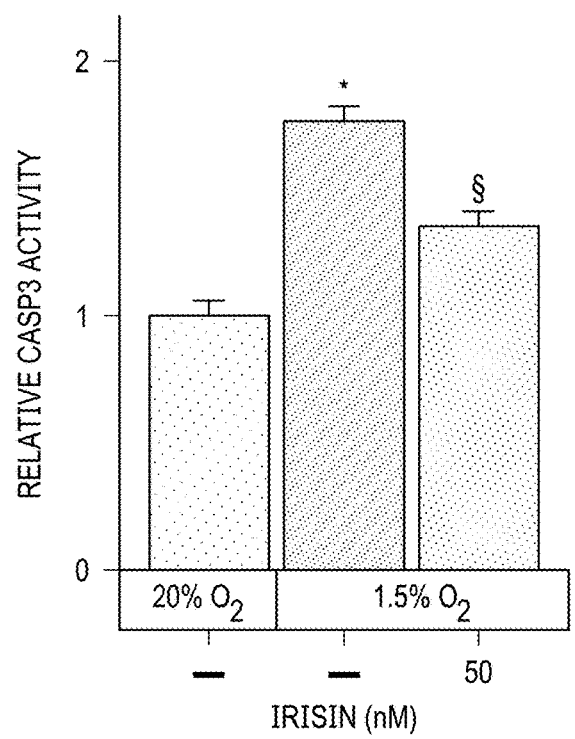

FIGS. 19A-19B show that excess generation of intracellular reactive oxygen species (ROS) in hypoxia decreases after irisin treatment (50 nM) in HTR-8/SVneo cells (FIG. 19A, top panels). Interaction between APAF1 and cytochrome C (an early step of apoptosis) decreases significantly, as visualized by in situ proximity ligation assay (PLA) technology (FIG. 19A, bottom panels). This process coincides with the inhibition of caspase-3 activity, as confirmed by specific fluorogenic substrates Ac-DEVD-AMC (FIG. 19B). In FIGS. 19A-19B, n=3, *p<0.05 (no-treatment normoxia versus no-treatment hypoxia), § p<0.05 (irisin treatment versus no-treatment hypoxia), and the scale bars are 50 μm.

Figure 20A:
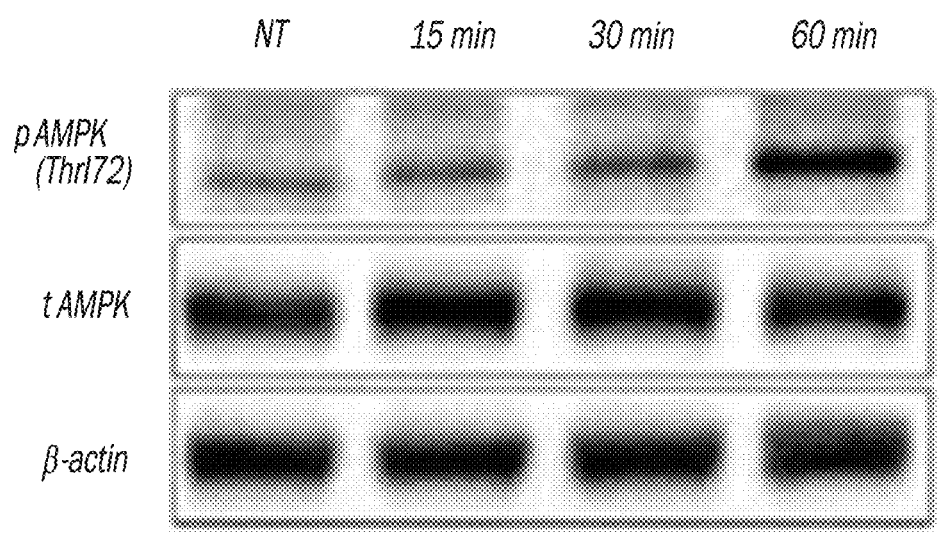
Figure 20B:
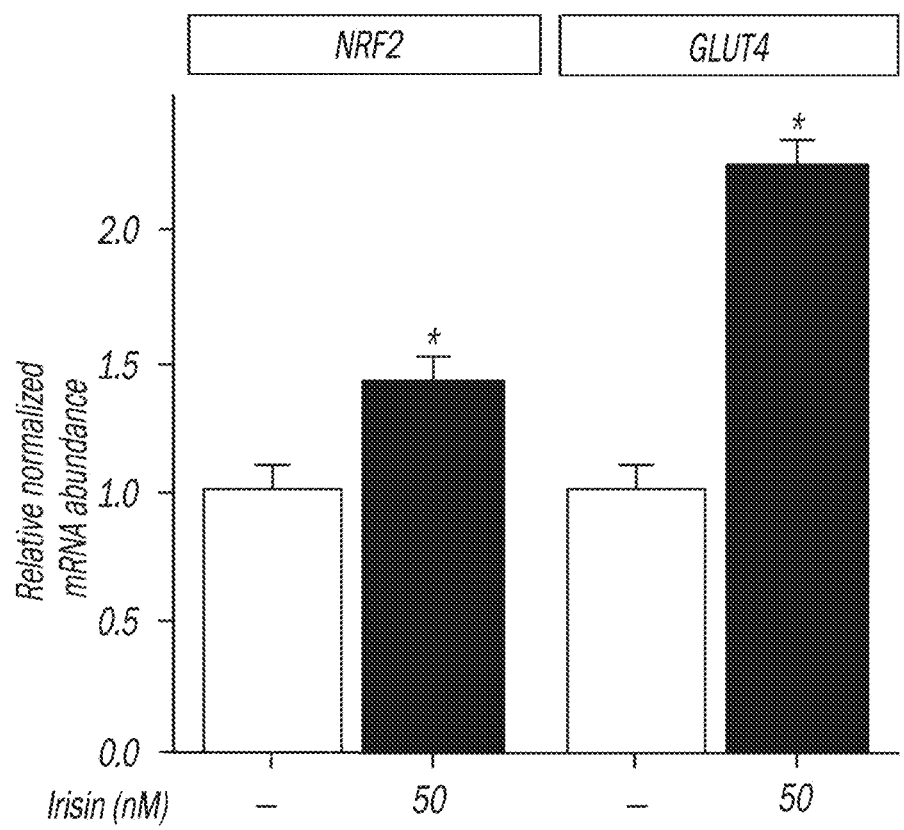

FIGS. 20A-20B show that irisin induces AMPK activity and NRF2 and GLUT4 overexpression. Irisin treatment (50 nM) induces AMPK activity (phosphorylation at Thr172) in HTR-8/SVneo trophoblast cell lines as early as 30 minutes and peaks at 1 hour (FIG. 20A) followed by (after 3 hours) overexpression of NRF2 and GLUT4 (a known downstream gene controlled by irisin; FIG. 20B). In FIGS. 20A-20B, n=3 and *p<0.05.

Figure 21:
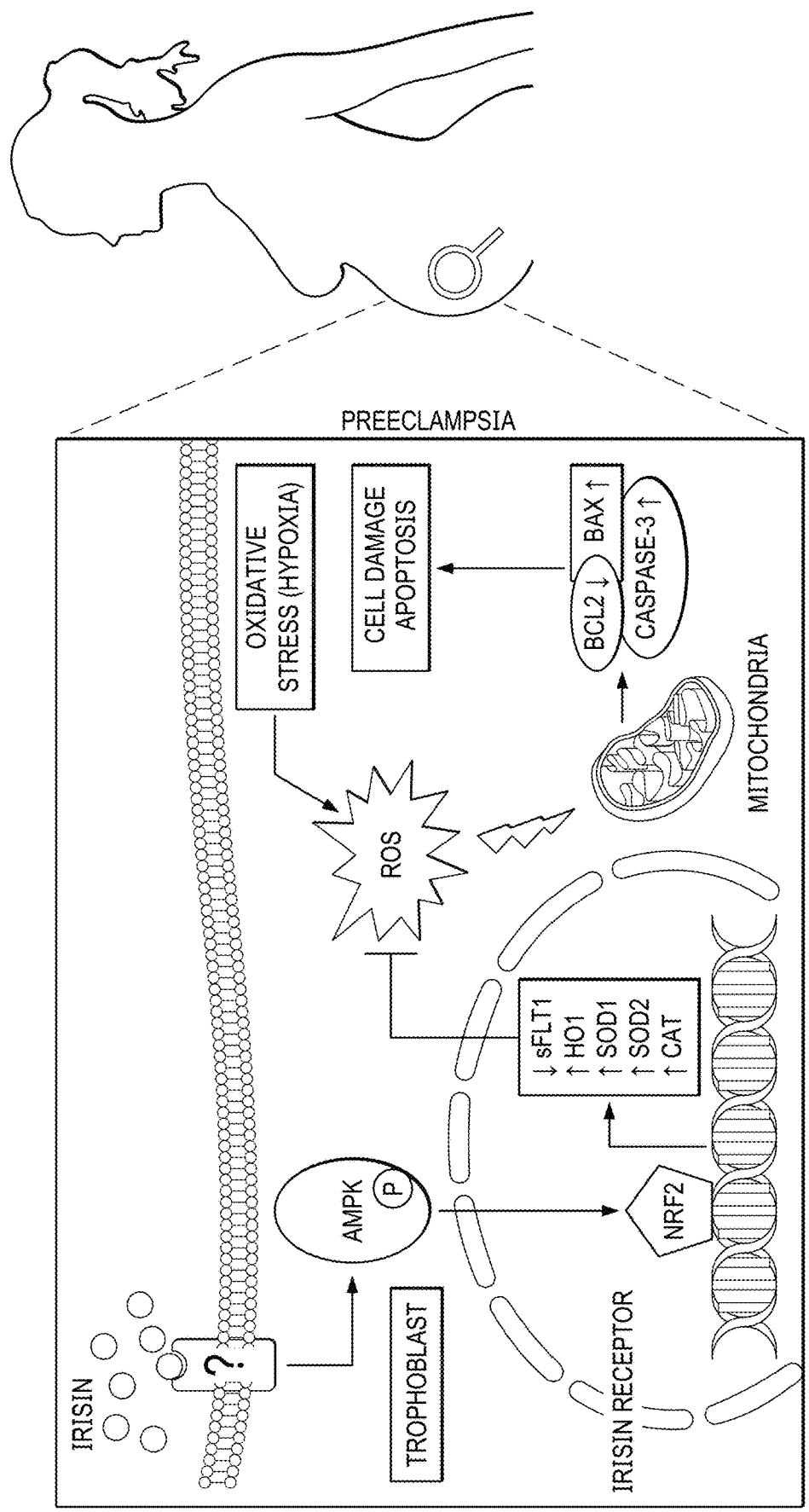

FIG. 21 is an illustration showing that during preeclampsia, the excess amount of intracellular ROS damages mitochondria in the placental trophoblast cell by activating intrinsic apoptosis pathways and causes maternal endothelial dysfunction by increased production of anti-angiogenic sFLT1 and others. It is believed that irisin, via a receptor, can interfere in this process by up-regulation/nuclear translocation of NRF2 via AMPK pathway activation. NRF2 transcriptional activity attenuates oxidative stress damage in both maternal and fetal compartments by inducing antioxidant enzymes (HO1, SODs, CAT) and suppressing anti-angiogenic sFLT1.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

Placental dysfunction, also referred to herein as "placental insufficiency" and "placental insufficiency syndrome," occurs during pregnancy when a placenta does not properly develop or is damaged and is characterized by the inability of the placenta to deliver to a fetus an adequate supply of nutrients and oxygen, which are crucial for the normal development of the fetus. As such, fetuses receiving insufficient levels of oxygen and/or nutrients can suffer metabolic changes, hormonal changes, hematologic changes, immunological changes, cardiovascular changes, behavioral changes, or combinations thereof and are at risk of developing metabolic disease. In turn, abnormal placental function can affect maternal health, resulting in, for example, hypertension, renal failure, seizures, and in the worst cases, death. Trophoblast apoptosis and dysregulation of energy homeostasis pathways are hallmarks of the placental pathophysiology. Placental dysfunctions include preeclampsia, oligohydramnios (i.e., lower than normal amniotic fluid), intrauterine growth restriction, abnormal placental growth, abnormal angiogenesis, increased (i.e., abnormal) apoptosis, and/or increased (i.e., abnormal) oxidative stress. Placental dysfunctions can result in pre-term birth, birth defects, miscarriage, or stillbirth.

The myokine irisin is a soluble peptide hormone released by the cell after proteolytic cleavage from the full-size, membrane-bound protein, FNDC5. Irisin promotes adipose tissue browning to increase energy levels and fuel metabolism in response to exercise. In normal pregnancy, irisin levels increase with gestation. In preeclamptic women, irisin levels are significantly reduced compared to healthy pregnant women. As shown in the examples, the human placenta expresses irisin and its receptors. Therefore, in accordance with the current technology, supplementing placentas with irisin improves placental and maternal blood vessel function and, in turn, placental endothelial function under pathological conditions.

The current technology provides a method of treating or inhibiting the progression of placental insufficiency syndromes in a subject (a human or non-human mammal) in need thereof. The method comprises administering to the subject a therapeutically effective amount of a composition comprising irisin. As used herein, the term "therapeutically effective amount" means an amount of a compound that, when administered to a subject having a placental dysfunction or suspected of having a placental dysfunction or an associated condition, is sufficient, either alone or in combination with additional therapies, to effect treatment for the placental dysfunction or the associated condition. The "therapeutically effective amount" will vary depending on, for example, the compound, pharmaceutical composition or pharmaceutical dosage form, the condition treated and its severity, and the age and weight of the patient to be treated. In various aspects, a therapeutically effective amount of the composition provides an irisin dose of greater than or equal to about 0.1 mg/kg of the subject to less than or equal to about 1000 mg/kg of the subject.

The composition comprising irisin optionally further comprises a pharmaceutically acceptable carrier or excipient. The term "pharmaceutically acceptable carrier" or "pharmaceutically acceptable excipient" refers to any and all solvents, dispersion media, binders, preservatives, antioxidants, coatings, isotonic and absorption delaying agents, and the like that are compatible with pharmaceutical administration. The term "aqueous carrier" refers to a pharmaceutically acceptable carrier in which the solvent is water.

Figure 1:
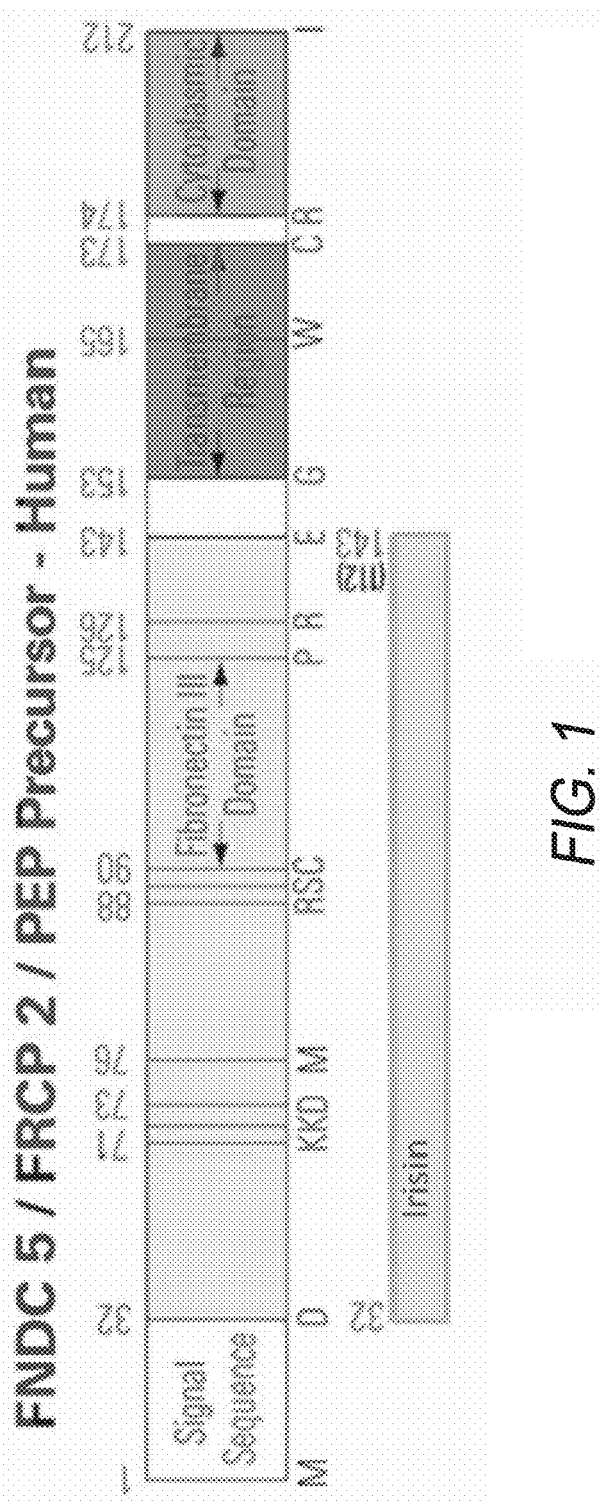
FIG. 1 shows the amino acid and domain sequences of FNDC5.

Irisin is a cleavage product of FNDC5, which has the amino acid sequence provided as SEQ ID NO:1. Irisin has the amino acid sequence provided as SEQ ID NO:3. FIG. 1 shows the domain structure of FNDC5 and corresponding sequences are provided in Table 1.

NO:3, a functional fragment thereof, or a fragment thereof. In some aspects, the amino acid sequence has an identity that is greater than or equal to 80%, greater than or equal to 85%, greater than or equal to 90%, greater than or equal to 95%, or 100% identical with the amino acid sequence provided as SEQ ID NO:3. The term "identity" as used herein refers to the degree of similarity between two amino acid sequences. An alignment of the two sequences is performed by a suitable computer program. The number of matching amino acids is divided by the total number of amino acids and multiplied by 100 to obtain a percent identity. For example, if two 120 amino acid sequences had 90 matched amino acids, they would be 75% identical. If the two compared sequences are of different lengths, the number of matches is divided by the shorter of the two lengths. For example, if there are 100 matched amino acids between 200 and about

TABLE 1

Amino acid sequences of FNDC5 and irisin.

| Domain | Amino Acids Relative to FNDC5 | SEQ ID NO: | Amino Acid Sequence |
| --- | --- | --- | --- |
| Entire FNDC5 | 1-212 | 1 | MHPGSPSAWPPRARAALRLWLGCVCFALVQA DSPSAPVNVTVRHLKANSAVVSWDVLEDEVVI GFAISQQKKDVRMLRFIQEVNTTTRSCALWDLE EDTEYIVHVQAISIQGQSPASEPVLFKTPREAEK MASKNKDEVTMKEMGRNQQLRTGEVLIIVVVLF MWAGVIALFCRQYDIIKDNEPNNNKEKTKSASE TSTPEHQGGGLLRSKI |
| Signal Sequence | 1-31 | 2 | MHPGSPSAWPPRARAALRLWLGCVCFALVQA |
| Irisin | 32-143 | 3 | DSPSAPVNVTVRHLKANSAVVSWDVLEDEVVI GFAISQQKKDVRMLRFIQEVNTTTRSCALWDLE EDTEYIVHVQAISIQGQSPASEPVLFKTPREAEK MASKNKDEVTMKE |
| Spacer | 144-152 | 4 | MGRNQQLRT |
| Transmembrane Region | 153-173 | 5 | GEVLIIVVVLFMWAGVIALFC |
| Cytoplasmic Domain | 174-212 | 6 | RQYDIIKDNEPNNNKEKTKSASETSTPEHQGG GLLRSKI |

The terms "protein," "polypeptide," "peptide," and "amino acid sequence" as referred to herein are used interchangeably to refer to compounds comprising amino acids joined via peptide bonds. A "protein" encoded by a gene is not limited to the amino acid sequence encoded by the gene, but includes post-translational modifications of the protein. The term "amino acid sequence" as used herein refers to an amino acid sequence of a protein molecule; the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from a nucleic acid sequence encoding the protein. The deduced amino acid sequence from a coding nucleic acid sequence includes sequences which are derived from the deduced amino acid sequence and modified by post-translational processing, where modifications include, but are not limited to, glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

In some aspects, the amino acid sequence of irisin includes a sequence that is substantially similar to SEQ ID 400 amino acid proteins, they are 50% identical with respect to the shorter sequence. If the shorter sequence is less than 150 bases or 50 amino acids in length, the number of matches are divided by 150 (for nucleic acid bases) or 50 (for amino acids) and multiplied by 100 to obtain a percent identity. The term "equivalent residue position" as used herein is a position in an irisin protein that is functionally equivalent to a residue position of a different irisin protein. The terms "amino acid substitutions" and "amino acid variants" as used herein refer to preferable substitutions of a single amino acid residue for another amino acid residue at any position within the protein. Substitutions, deletions, insertions, or any combinations thereof can be combined to arrive at a final construct.

The terms "protein," "polypeptide," "peptide," and "amino acid sequence" include compositions of the present technology that also include "analogs" or "conservative variants" and "mimetics" ("peptidomimetics") with structures and activity that substantially correspond to the exemplary sequences. Thus, the terms "conservative variant," "analog," or "mimetic" also refer to a polypeptide or peptide which has a modified amino acid sequence, such that the change(s) do not substantially alter the polypeptide's (conservative variant's) structure and/or activity (e.g., ability to activate AMPK, etc.), as defined herein. These include conservatively modified variations of an amino acid sequence (i.e., amino acid substitutions, additions, or deletions of those residues that are not critical for protein activity) or substitution of amino acids with residues having similar properties (e.g., acidic, basic, positively or negatively charged, polar or non-polar, etc.), such that the substitutions of even critical amino acids do not substantially alter structure and/or activity.

Conservative substitution tables providing functionally similar amino acids are well known in the art. For instance, one exemplary guideline to select conservative substitutions includes (original residue followed by exemplary substitution): ala/gly or ser, arg/lys, asn/gln or his, asp/glu, cys/ser, gln/asn, gly/asp, gly/ala or pro, his/asn or gln, ile/leu or val, leu/ile or val, lys/arg or gln or glu, met/leu or tyr or ile, phe/met or leu or tyr, ser/thr, thr/ser, trp/tyr, tyr/trp or phe, and val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). One of skill in the art will appreciate that the above-identified substitutions are not the only possible conservative substitutions. For example, for some purposes, one may regard all charged amino acids as conservative substitutions for each other, whether they are positive or negative. In addition, individual substitutions, deletions, or additions that alter, add, or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides of the present technology (e.g., ability to active AMPK). The mimetic can either be entirely composed of synthetic, non-natural analogues of amino acids or be a chimeric molecule of partly natural peptide amino acids and partly non-natural analogs of amino acids. The mimetic can also incorporate any amount of natural amino acid conservative substitutions, as long as such substitutions also do not substantially alter the mimetic's structure and/or activity. As with polypeptides of the present technology which are conservative variants, routine experimentation will determine whether a mimetic is within the scope of the technology, i.e., that its structure and/or function is not substantially altered.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry—i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds, or coupling means, such as, e.g., glutaraldehyde, N-hydroxysuccinimide esters, bifunctional maleimides, N,N'-dicyclohexylcarbodiimide (DCC), or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester. A polypeptide can also be characterized as a mimetic by containing all or some non-natural residues in place of naturally occurring amino acid residues, non-natural residues are well described in scientific and patent literature.

The irisin can be isolated from mammalian cells as a naturally expressed protein, or it can be generated recombinantly in prokaryotic or eukaryotic cells and subsequently isolated. However, the irisin, especially in embodiments where the irisin is recombinant irisin, can also include a tag used to isolate the irisin from a cell lysate or to localize the irisin to a predetermined location within a placental cell. In some aspects, the irisin includes a tag that can be removed, for example, during or after purification. Exemplary tags include flag tag, calmodulin, His-tag, and combinations thereof, as non-limiting examples. Tags can optionally be removed by any means known in the art, for example, by a serine thrombin protease which specifically cleaves peptides at a thrombin recognition sequence that is used as a linker. In some aspects, the irisin remains active with a tag and the tag remains coupled to the irisin during the administration.

The administering can be performed by any method or route known in the art, including orally, sublingually, intravenously, intramuscularly, intravaginally, subcutaneously, or directly to the placenta of the subject, as non-limiting examples. In some aspects, the method further comprises administering a therapeutically effective amount of an adjunct agent to the subject. The adjunct agent can be simultaneously co-administered with the composition comprising irisin, optionally as a component in the composition comprising irisin, or the adjunct agent can be administered separately. The adjunct agent can treat the placental dysfunction or an indication secondary to the placental dysfunction. For example, when the placental dysfunction is preeclampsia, the adjunct agent can be an antihypertensive agent.

The current technology also provides a method of treating a subject (a human or non-human mammal) suspected of having a placental dysfunction. The method comprises obtaining a tissue or cell sample comprising a plurality of cells originating from the subject's placenta or cervix and determining a first irisin level expressed from the plurality of cells. The irisin level can be determined through methods known in the art, such as by quantitative polymerase chain reaction (qPCR), Western blotting with a monoclonal or polyclonal antibody that specifically recognizes irisin, mass spectrometry, or using a combination of these methods.

The method then comprises comparing the first irisin level with a second irisin level provided from a normal control. In some aspects, the normal control is a second plurality of cells originating from a placenta or cervix of either the same subject from a previous pregnancy at a corresponding gestation time or a different subject or plurality of subjects (in which case the second irisin level is an average level) at a corresponding gestation time. As used in context of the term "control", "normal" means that the subject from which the plurality of cells were isolated did not have a placental dysfunction, i.e., the cells were taken from the subject during a pregnancy without complications.

When the first irisin level is lower than the second irisin level, the method comprises administering to the subject a therapeutically effective amount of a composition comprising irisin. The administering and the composition comprising irisin are discussed above. In some aspects, the administering is performed when the first irisin level is at least about 5%, at least about 10%, at least about 15%, at least about 20%, or at least about 25% lower than the second irisin level.

The current technology yet further provides a method of treating a placenta by increasing trophoblast differentiation, increasing placental outgrowth, decreasing trophoblast apoptosis, decreasing oxidative stress, or combinations thereof. The method comprises contacting the placenta with irisin. In various aspects, the contacting the placenta with irisin comprises contacting the placenta with a composition comprising irisin, such as any composition described herein.

In some aspects, the placenta is in a human or non-human mammalian subject having a placental dysfunction, such as any placental dysfunction described herein. Here, the contacting the placenta with irisin results from previously administering (by any method or route discussed herein) a composition comprising the irisin to the subject. Unless administered directly to the placenta, the irisin is delivered to the placenta through an artery.

Embodiments of the present technology are further illustrated through the following non-limiting examples.

Example 1

Introduction

Placental insufficiency during pregnancy is characterized by the inability of the placenta to deliver an adequate supply of nutrients and oxygen to the fetus. This can result in diseases such as preeclampsia, intrauterine growth restriction, and pre-term birth. Trophoblast apoptosis and dysregulation of energy homeostasis pathways are hallmarks of the placental pathophysiology.

Irisin, the secreted cleavage product of FNDC5, is mainly known as an exercise-mediated myokine. Irisin induces adipose tissue browning upon exercise, increasing energy levels, decreasing apoptosis, and decreasing the effects of hypoxia. Irisin appears to activate the AMPK and Akt signaling pathways in endothelial cells known to be involved in placental pathogenesis. Circulating irisin levels are reduced in preeclampsia, and the overall role of irisin in placental function and pathology is unclear.

Figure 2:
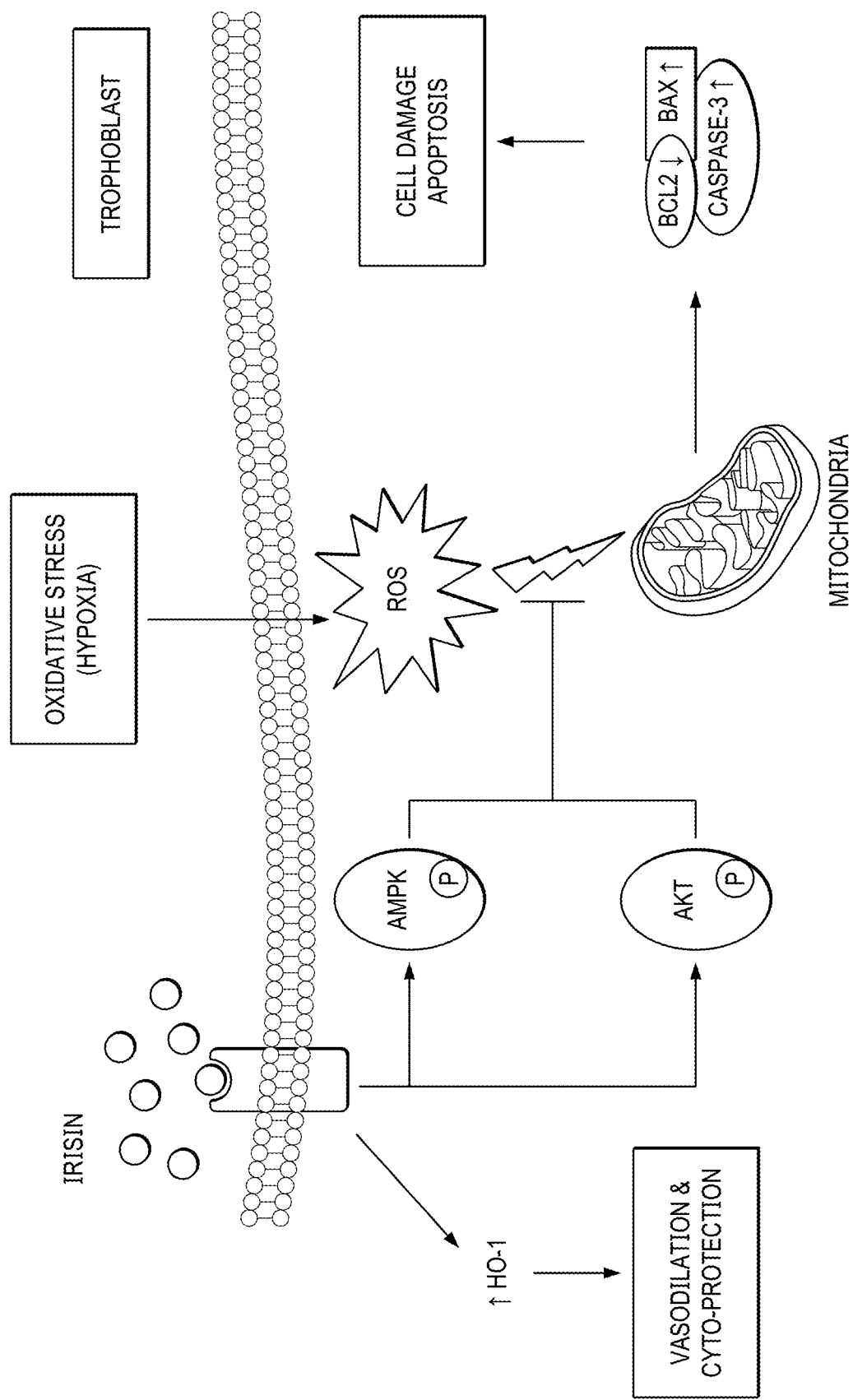
FIG. 2 is an illustration showing how irisin can minimize the formation of reactive oxygen species and decrease apoptosis in trophoblasts according to the current technology.

Irisin has a direct effect on placental physiology. In this example, trophoblast-like cell lines are used to mechanistically assess the effects of irisin on trophoblast apoptosis in an AMPK/Akt dependent manner under physiological and pathological conditions. FIG. 2 is a working model showing how irisin promotes cell function and inhibits apoptosis by inducing phosphorylation in trophoblast cells under physiological and pathological conditions.

Materials and Methods

Extravillous (HTR-8/SVneo) and villous (BeWo) trophoblast cell models are used to investigate the effects of irisin under physiological (20% O2) and pathological conditions (1.5% O2, followed by 20% O2). Cells are serum starved overnight and treated with 10 or 50 nM irisin for up to 24 hours (n=3 per group). Extracted proteins are analyzed by Western blot and mass spectrometry. To establish the mechanistic effects of irisin in the cell-based models, pAMPK and pAkt are measured by Western blot. Compound C (dorsomorphin), a highly specific antagonist of the AMPK pathway, is used to validate AMPK-dependent actions of irisin.

Results

FIG. 3 shows that irisin decreases hypoxia-induced apoptosis in BeWo trophoblast cells in a dose-dependent manner. BeWo trophoblast cells were cultured overnight in hypoxia (1.5% O2) followed by a 6 hour incubation in 20% O2 in absence (N/T: no treatment) or presence of irisin (10 or 50 nM). Apoptotic cells were detected by TUNEL assay. Apoptotic cells are shown in the top row and nuclei in the bottom row (size bars=100 µM).

Figures 4A, 4B:
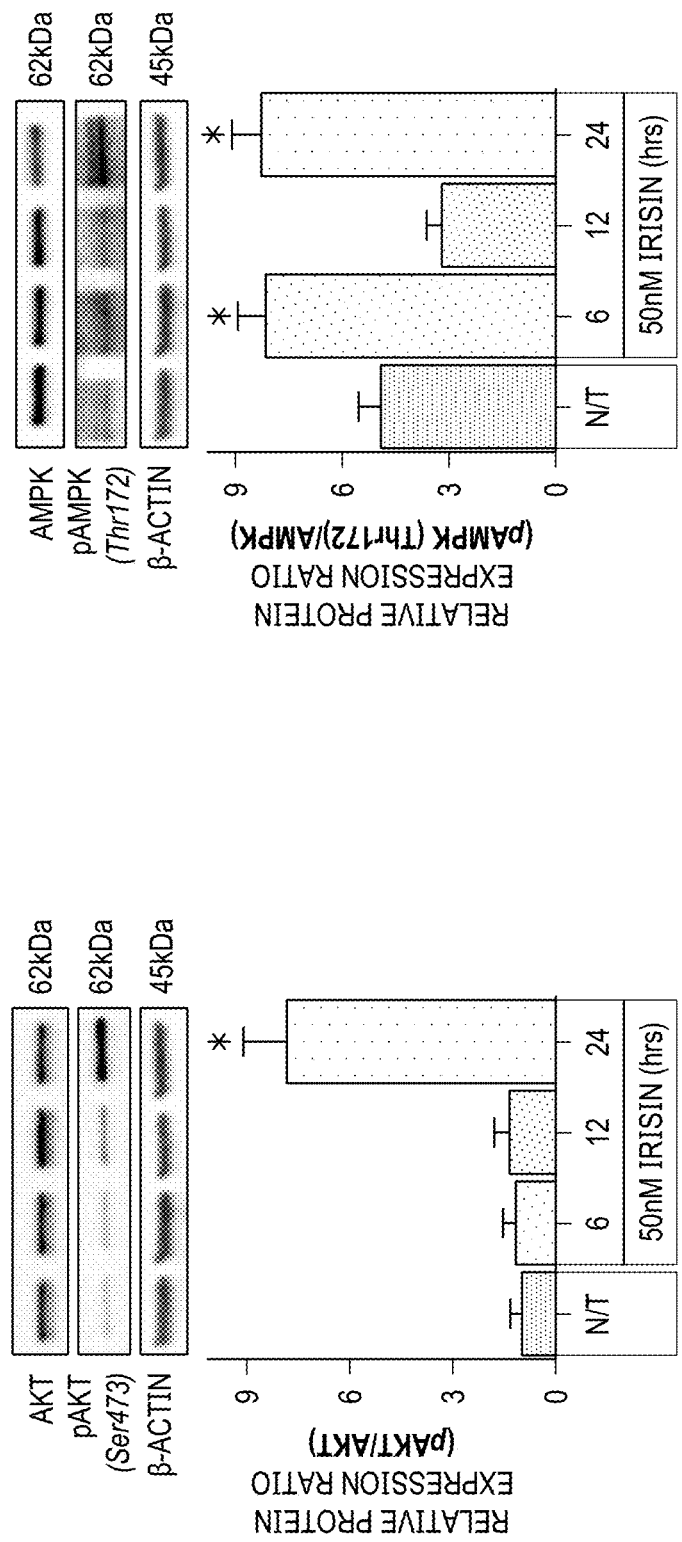
Figures 4C, 4D, 4E:
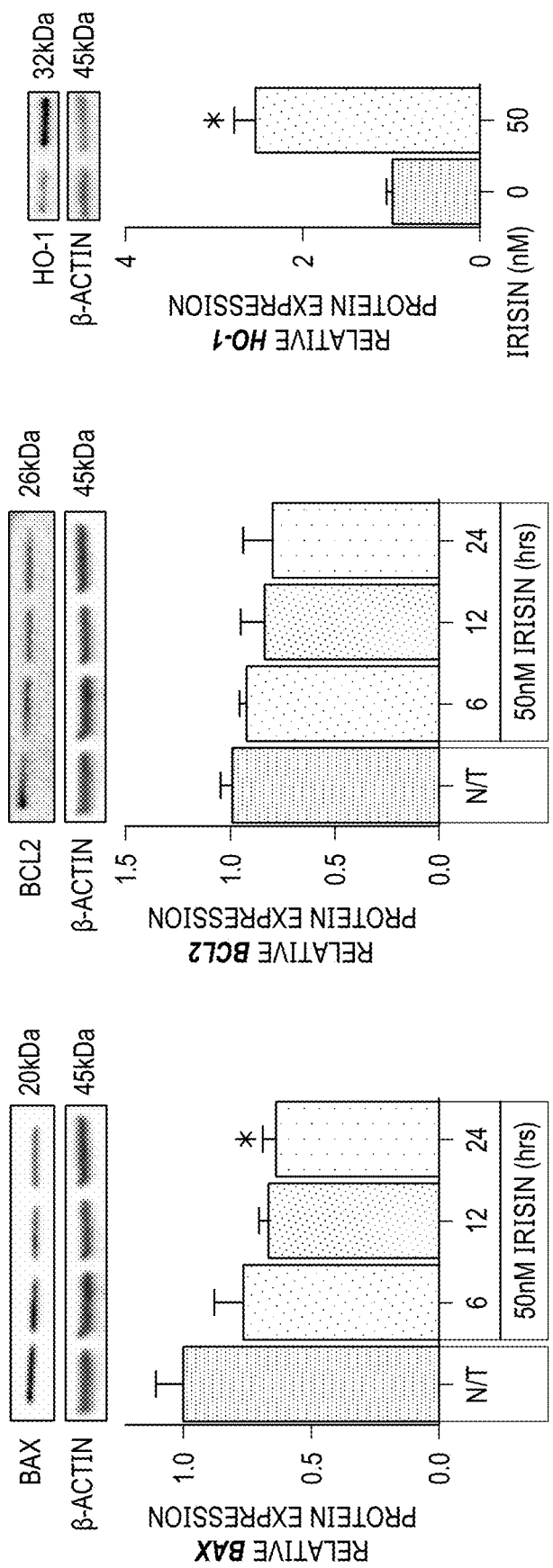

FIGS. 4A-4E show that irisin activates Akt and AMPK pathways, reducing pro-apoptotic BAX and inducing cytoprotective HO-1 expression in BeWo cells. Exposure to 50 nM irisin for up to 24 hours induces phosphorylation of Akt and AMPK, as shown in FIGS. 4A and 4B, respectively. FIG. 4C shows that pro-apoptotic BAX is reduced significantly at 24 hours, while FIG. 4D shows that BCL2 remains unchanged. FIG. 4E shows that cytoprotective HO-1 is significantly induced by irisin treatment (n=3, p<0.05).

FIGS. 5A-5B show that the effects of irisin on apoptosis are mediated via AMPK and blocked by compound C in hypoxia-treated BeWo cells. As shown in FIG. 5A, apoptosis (top row) occurs in non-treated cells (N/T) under hypoxic conditions compared to the normoxic control (N/T, 20%). Irisin treatment reduces apoptosis, which was blocked by compound C. Compound C alone under hypoxia results in increased apoptosis. The bottom row shows the merged image of nuclear DAPI staining and apoptotic cells. As shown in FIG. 5B, irisin treatment induces high phosphorylation levels of AMPK, which correlates with low levels of apoptosis observed from the TUNEL assay (FIG. 5A). Compound C blocks irisin-induced phosphorylation of AMPK. Compound C treatment alone reduces pAMPK (n=3, p<0.05).

FIGS. 6A-6E show a phosphoproteomic analysis of BeWo cells treated with irisin. Cells were treated with 50 nM irisin for 1 hour. Protein was extracted and phosphoproteins enriched using Pierce Phosphoprotein Enrichment Kit (Thermo Scientific Cat. No: 90003). Next, proteins were digested overnight at 37° C. with trypsin and LysC and loaded on a PepMap RSLC C18 column connected to a Tandem mass spectrometer. The resulting spectra was subjected to a database search using Proteome Discoverer (Version 2.2.0.388) and plotted. FIG. 6A shows a heat map of a hierarchical clustering of samples showing a distinct abundance pattern of phosphopeptides in irisin-treated cells. FIG. 6B is a volcano plot depicting change of phosphopeptides. All abundance ratios (fold changes) are log 2 transformed (x-axis) and plotted against the –log 10 transformed statistical significance (y-axis). From 727 curated phosphopeptides, those with at least two-fold increase (right; n=31) or decrease (left; n=16) by exposure to irisin with p<0.05 are indicated. FIG. 6C shows a functional analysis of irisin-induced phosphoproteome changes performed on an iPathwayGuide/Advaita platform, with the top five terms enriched in "Biological Pathways" identified. It is revealed that irisin significantly alters the abundances of phosphopeptides that belong to two metabolic pathways—"pyrimidine metabolism" (as shown in FIG. 6D) and "pentose and glucuronate interconversions" (as shown in FIG. 6E).

Discussion

Preeclampsia and other placental disorders are characterized by increased apoptosis and hypoxic stress. Until now, no treatments existed for placental insufficiency syndromes. The naturally occurring protein irisin shows direct effects on cell survival via AMPK/Akt pathways (FIGS. 3-5). Mass spectrometry shows that irisin affects metabolic pathways related to energy homeostasis in human trophoblasts (FIG.

6). Due to its biological properties, irisin holds promise as a target for the treatment of abnormal placentation.

Example 2

Summary

Irisin, a newly discovered adipokine, regulates differentiation and phenotype in different cell types, including myocytes, adipocytes and osteoblasts. Circulating irisin concentration is elevated throughout human pregnancy, but in adverse cases, such as preeclampsia and gestational diabetes mellitus, irisin level is reduced. Aberrant trophoblast differentiation is part of preeclampsia pathophysiology. To date, there are no data on the potential role of irisin in placental function and development or its contribution into placental pathology. Here, the effect of irisin on placental proliferation, differentiation, and function is assessed. First-trimester placental explants were collected and cultured with low (10 nM) or high (50 nM) physiological doses of irisin. Treatment with irisin increased both placental outgrowth (on Matrigel®) and trophoblast fusion index, dose dependently. By contrast, irisin reduced proliferation index and inhibited the expression of proliferation markers, including CCND3, CCNE1, MYBL2, and PCNA. The data also shows that AMPK activation increases in placenta after exposure to irisin. To determine whether AMPK pathway regulates the trophoblast differentiation induced by irisin, two trophoblast cell lines, HTR-8/SVneo and BeWo, were treated with irisin and/or a specific AMPK inhibitor (compound C). Irisin induced AMPK phosphorylation in HTR-8/SVneo cells. Integrin expression in HTR-8/SVneo cells switched from α6 to α1, and invasiveness increased upon addition of irisin, while AMPK inhibitor attenuated irisin-stimulated cell fusion (in BeWo), cell migration/invasion (in HTR-8/SVneo), as well as villous (GCM1, SYN1, PSG1, and HCGB) and extravillous (HSP21, ITGA1, MMP12, and PGF) trophoblast differentiation markers. These findings indicate that exposure to irisin promotes differentiation and improves trophoblast function in the human placenta. As such, irisin signaling represents a therapeutic target for conditions associated with placental pathologies, such as preeclampsia.

Introduction

Despite the known association between peripheral irisin levels and both normal and complicated pregnancies, the function of the peptide hormone, irisin, in the modulation of placenta function and/or pathology has remained unknown. The effects of irisin on human trophoblast differentiation and function using first-trimester placental explants and trophoblast-like cell lines are elucidated here. Whether the mechanism is regulated by the AMPK signaling pathway is also discussed.

Materials and Methods

Placental tissue collection. First-trimester (10 to 12 weeks of gestation) placental tissues (n=5) were obtained with written informed consent from healthy pregnant women undergoing elective termination of pregnancy. The Institutional Review Board of Wayne State University approved all consent forms and protocols used, which abide by the National Institutes of Health (NIH) research guidelines. The collected tissues were washed and transported to the laboratory in ice-cold Hank's balanced salt solution and processed within a maximum of 2 hours after collection. Upon arrival, tissues were snap-frozen in liquid nitrogen for further analysis. For ex vivo modeling, individual clusters of villous trees were dissected under a stereomicroscope and cultured in 1 ml of Dulbecco's modified Eagle's medium/Ham's F-12 nutrient mixture (DMEM/F-12; 1:1; Life Technologies; Grand Island, NY) containing 10% fetal bovine serum (FBS; Life Technologies) and 1% Gibco™ antibiotic-antimycotic. The explants were maintained overnight at either 8% or 1.5% $O_2$ with 5% $CO_2$ at 37° C. Placental explants were cultured in a medium supplemented with low (10 nM) or high (50 nM) physiological doses of active recombinant irisin (Enzo Life Sciences, Farmingdale, NY).

Human trophoblast cell culture. The HTR-8/SVneo and BeWo cell lines were cultured in a mixture of DMEM/F-12 (1:1) containing 10% FBS. The culture medium was changed every two to three days, and cells were passaged with trypsin-ethylenediaminetetraacetic acid (EDTA) solution (Life Technologies). To examine the effect of irisin on trophoblast differentiation, the cells were treated with 10 nM or 50 nM of recombinant irisin (Enzo Life Sciences).

Immunofluorescence. Following treatments, placental villi were labeled for immunohistochemistry, as known in the art. Briefly, the placental villi were fixed in 4% paraformaldehyde in phosphate-buffered saline (PBS), embedded in paraffin, sectioned at 5 µm thickness, and mounted on glass slides. After deparaffinization and rehydration, sections were blocked with 3% bovine serum albumin (BSA) in PBS followed by incubation overnight at 4° C. with anti-pregnancy-specific β-1-glycoprotein 1 (PSG1; Abcam; Cambridge, UK). The primary antibody was visualized with 0.3 µg/ml fluorescein (fluorescein isothiocyanate [FITC])-conjugated secondary antibody (Jackson ImmunoResearch, West Grove, PA) and counterstained with 5 µg/ml DAPI (EMD Biosciences, Billerica, MA). After experimentation, the BeWo and HTR-8/SVneo cell cultures were fixed in 4% paraformaldehyde in PBS for 10 minutes, permeabilized for 7 minutes with 0.01% Triton X-100 in PBS, blocked in 3% BSA in PBS for 1 hour at room temperature, and incubated overnight at 4° C. with 1 µg/ml of mouse monoclonal antibodies against the E-cadherin (Abcam) or integrin subunits α1 or α6 (Upstate Biotechnology, Lake Placid, NY). Tetramethylrhodamine (TRITC) or FITC-conjugated donkey anti-rabbit secondary antibody (Jackson ImmunoResearch) was applied for 2 hours at room temperature. Hoechst 33342 was used to stain nuclei. Slides were analyzed in an Eclipse 90i epifluorescence microscope (Nikon, Melville, NY).

Cell fusion assay. Immunofluorescence microscopy was also performed to assess cell fusion in accordance with known methods. Briefly, the number of nuclei in syncytia and the total number of DAPI-labeled nuclei were counted from four non-overlapping microscopic fields, and the fusion index was calculated as (number of nuclei in syncytium/total number of nuclei)×100. The calculation was performed by averaging counts for four fields of each specimen from duplicate samples of at least three independent experiments.

Invasion assay. The invasion assay was performed as is known in the art. Briefly, a cluster of chorionic villi was dissected and incubated overnight on Matrigel® (BD Biosciences, Franklin Lakes, NJ) in DMEM/F-12+10% FBS medium in a 24-well culture plate to allow attachment. After 1 day, the medium was replaced with either new medium (nontreatment control) or medium supplemented with low or high physiological irisin concentrations that are seen during pregnancy (10 nM or 50 nM). Villous explants were cultured for 48 hours in 8% $O_2$ and 5% $CO_2$ at 37° C. The adherence of villous explants to Matrigel® and protrusion and migration of EVT cells were imaged after 48 hours by light microscopy. The size of EVT outgrowth from the distal end of the villous tips into the matrix was measured for four villi of each explant, and the average of eight measurements for each explant was used for analysis. HTR-8/SVneo cells (100,000 per well) were also cultured for 72 hours on Matrigel® (BD Biosciences) in 6.5-mm Transwell® inserts (Corning, Acton, MA), as is known in the art. Cells that invaded the Matrigel® and populated the lower chamber were detached using the trypsin-EDTA solution, fixed, and counted.

Protein extraction and immunoblotting. Protein extraction from tissues (20 to 30 mg) was performed as known in the art. Protein concentration was determined with BCA™ protein assay reagent (Thermo Fisher Scientific; Rockford, IL) according to manufacturer instructions. Equal protein amounts (35 µg) were denatured (8 minutes, 95° C.) in Laemmli sample buffer (Bio-Rad Laboratories; Hercules, CA) and separated using sodium dodecyl sulfate-polyacrylamide gel electrophoresis, with subsequent semi-dry transfer (Trans-Blot®; Bio-Rad Laboratories) to a polyvinylidene difluoride membrane. The membranes were blocked with 5% nonfat dry milk in 1× Tris-buffered saline containing 0.05% Tween-20 and incubated overnight at 4° C. with anti-GCM1 (1:5,000; Aviva, San Diego, CA), anti-AMPKα (1:1,000; Cell Signaling Technology, Danvers, MA), and anti-phospho-AMPKα (Thr172; 1:1,000; Cell Signaling Technology) primary antibodies. Subsequently, membranes were incubated with horseradish peroxidase-conjugated secondary antibodies for 1 hour at room temperature and developed with Western Lightning® ECL Pro (PerkinElmer, Waltham, MA). Signals were visualized using a ChemiDoc™ Imaging System (Bio-Rad Laboratories) and Image Lab Version 5.1 software (Bio-Rad Laboratories). Densities of immunoreactive bands were measured as arbitrary units by ImageJ software (NIH, Bethesda, MD). Protein levels were normalized to a housekeeping protein (s-actin; 1:20,000; Abcam).

Statistical analysis. All experiments were performed at least three times. A one-way analysis of variance and a subsequent Tukey's post hoc test were performed to analyze differences between cohorts. An effect was considered significant when $p<0.05$. For arbitrary units, results were calculated relative to nontreatment (NT) controls (set as 1) and presented as mean±standard error of the mean.

Results

EVT migration and invasion are induced by irisin in the first-trimester human placenta. To investigate the effect of irisin on EVT differentiation in the human first-trimester placenta, placental explants were exposed to low (10 nM) or high (50 nM) physiological concentrations of recombinant irisin, and migration and extravillous outgrowth formation were examined. Anchoring villi exposed to irisin developed large EVT outgrowths from their tips (FIGS. 7A-7F). The outgrowth length (mean±standard error of the mean) was significantly higher in placental explants treated with irisin doses of 10 nM (352.6±18.4 µM) and 50 nM (384.6±21.2 µM) than in NT controls (201.4±140.5 µM; FIG. 7G). Irisin treatment of first-trimester placental explants also increased active pAMPK levels, while total AMPK levels did not change with treatment (FIG. 7H).

Irisin promoted invasion and induced extravillous differentiation in HTR-8/SVneo trophoblast cells. To analyze differentiation in trophoblast cells, first-trimester human EVT-like trophoblast cells, HTR-8/SVneo, were cultured on Matrigel©-coated Transwell® inserts and exposed to low (10 nM) and high (50 nM) concentrations of irisin. Irisin significantly stimulated the invasion of HTR-8/SVneo cells, as shown by the number of cells invading through Matrigel® (mean±standard error of the mean) being significantly higher in irisin concentrations of 10 nM (15,965±735; $p<0.05$) and 50 nM (17,238±1,005; $p<0.05$) than in NT controls (4,570±352; FIGS. 8A and 8B). Integrin switching from $\alpha 6\beta 4$ to $\alpha 1\beta 1$ is a marker for extravillous differentiation. Irisin induced integrin switching (differentiation) in the trophoblast cell line. Irisin-treated cells expressed higher levels of integrin $\alpha 1$ and lower levels of $\alpha 6$ (mean stain intensity [arbitrary]±standard error of the mean) at 10 nM (integrin $\alpha 1$, 50.7±2.1; integrin $\alpha 6$, 13.4±3.4) and 50 nM (integrin $\alpha 1$, 55.7±2.8; integrin $\alpha 6$, 19.3±2.7) compared to NT controls (integrin $\alpha 1$, 9.4±2.4; integrin $\alpha 6$, 52.5±4.0; FIG. 8C). Additionally, irisin induced AMPK phosphorylation in a dose-dependent manner in HTR-8/SVneo cells (FIG. 8D).

Irisin induction of EVT differentiation in trophoblasts depends on AMPK activation. To validate the involvement of AMPK signaling in irisin-mediated EVT differentiation, HTR-8/SVneo cells were pretreated with 10 µM of compound C, an adenosine triphosphate (ATP)-competitive antagonist of AMPK, for 2 hours before being exposed to 50 nM of irisin for 24 hours. The AMPK-activating effects of irisin were abolished in the presence of compound C. Exposure to compound C blocked the overexpression of pAMPK compared to irisin alone (FIG. 9A), showing that irisin exerts its function in trophoblast cells through the phosphorylation of AMPK. Peripheral loss of integrin $\alpha 6$ in trophoblasts is an early marker for EVT differentiation that enables cells to migrate into the maternal tissue compartment. Antagonizing AMPK with compound C also attenuated the irisin-induced downregulation of integrin $\alpha 6$ (FIG. 9B). The results were further confirmed using first-trimester tissues. Placental explants were incubated for 24 hours with irisin 50 nM alone or were pretreated and cocultured with 10 µM of compound C on Matrigel®. Microscopy examination illustrated that compound C pretreatment of the placental explants blocked irisin-mediated EVT differentiation and Matrigel® invasion (FIG. 9C).

Irisin facilitates villous CTB differentiation and STB formation in the human placenta. To determine whether irisin can alter villous CTB differentiation, first-trimester human placental explants were incubated with low (10 nM) and high (50 nM) physiological concentrations of irisin. The formation of STB cells was quantified by the calculation of a fusion index (see above). Comparing the fusion indices of control placental explants (16.6±0.98%) to those of the explants treated with irisin 50 nM (25.7±1.5%) demonstrated significant increases in fusion levels in response to irisin treatment (FIG. 10A). The differentiation marker PSG1 was upregulated by irisin, as confirmed by immunofluorescence microscopy and PSG1 localization in the syncytium (FIG. 10B). Protein expression of the differentiation marker GCM1 (1.35±0.12) was also significantly increased in explants treated with irisin 50 nM than in NT controls ($p<0.05$; FIG. 10C).

Irisin mediates villous CTB differentiation through AMPK activation. To confirm the role of irisin in AMPK-mediated CTB differentiation, the villous CTB-like cell line BeWo was exposed to irisin (10 and 50 nM) for 72 hours. Irisin induced formation of multinucleated syncytia, displaying a dose-dependent loss of cell wall-localized E-cadherin (FIG. 11A) compared to NT controls. These observations coincided with an increase in pAMPK and GCM1 protein expression shown by Western blot analysis (FIGS. 11B and 11C). To verify whether irisin enhances CTB differentiation via AMPK activation, BeWo cells were preincubated with compound C for 2 hours and treated with irisin 50 nM for 24 hours. Microscopic analysis revealed that inhibition of AMPK counteracted the stimulating effects of irisin on syncytium formation (FIG. 11D). Coaddition of compound C markedly inhibited the stimulation of AMPK activation by irisin (FIG. 11E).

Discussion

The fact that irisin levels are higher in maternal circulation than in nonpregnant women and are constantly elevated throughout gestation raises the question of whether this myokine/adipokine has a significant role in the establishment and maintenance of a healthy pregnancy. Trophoblast differentiation is critical to normal placental development and pregnancy outcomes. Abnormal trophoblast differentiation controlled by kinase signaling pathways, including the phosphoinositide 3-kinase/Akt and AMPK pathways, are associated with placental disorders, such as preeclampsia. It is demonstrated here that irisin induces EVT differentiation, migration, and invasion. Additionally, irisin promotes villous CTB differentiation and syncytium formation. These results are consistent with previous reports that irisin promoted neural, osteoblast, and adipocyte differentiation, although the underlying mechanisms remain poorly understood. Recent studies suggest that low levels of irisin in pregnant women with preeclampsia are associated with placental abnormalities and insufficiency. Preeclampsia is characterized by reduced EVT invasion and spiral artery remodeling, as well as abnormal villous CTB fusion and syncytialization. The present example shows that irisin has a role in trophoblast differentiation during the first trimester of pregnancy. Irisin expression and secretion are reduced under hypoxic conditions. Hypoxia is a hallmark of placental insufficiencies, especially in sPE. sPE placentas show signs of hypoxia and/or hypoxia/reoxygenation injury, which is mostly attributed to the unsuccessful transformation of the spiral arteries that leads to episodes of hypoxia or H/R. As the result of hypoxia, several molecular pathways controlling cell survival, angiogenesis and mitochondrial function are severely affected. In preeclampsia, acute hypoxic stress activates oxygen-sensitive transcriptional factors, such as HIF1α. Constitutive expression of HIF1α in adipose tissue significantly inhibits the expression of peroxisome proliferator-activated receptor-gamma coactivator-1 (PGC1α), a transcriptional activator that promotes FNDC5 (irisin precursor) expression. This may explain the lower peripheral irisin in preeclampsia; however, the specific role of HIF1α-PGC1a in the modulation of FNDC5 expression and irisin secretion, is not well understood. More studies are needed to evaluate the contribution of oxygen tension and hypoxia to altered circulating concentrations of irisin in pregnancy complications such as preeclampsia.

As shown above, irisin promotes EVT differentiation and invasion. It has previously been shown that irisin induces cell invasion in human hepatocellular carcinoma. In contrast, other studies reveal that irisin suppresses migration and invasion in osteocarcinoma and lung cancer cells. Therefore, irisin appears to modulate cell differentiation, migration, and invasion properties in a tissue-dependent manner. In trophoblasts, EVT differentiation is initiated by an altered expression of cadherins and integrins. Failure of these molecular events is associated with placenta-insufficiency syndromes. Transient downregulation of E-cadherin, the adherens junction protein, is an early marker of EVT differentiation. Here, it is shown that irisin dose-dependently stimulates EVT invasion, accompanied by the downregulation of E-cadherin. The cadherins, particularly E-cadherin, have important roles in CTB formation and EVT differentiation through the regulation of cell adhesion and through cell invasion via an epithelial-mesenchymal transition (EMT) process. During the first and second trimesters of pregnancy, to invade and remodel uterine spiral arteries for the establishment of placental blood supply, EVTs undergo EMT to acquire migratory and invasive capabilities. In preeclampsia, the overexpression of placental E-cadherin is accompanied by limited EVT differentiation and shallow invasion.

Irisin also altered the placental integrin expression profile. Integrins are the major physical links between the cytoskeleton and the extracellular matrix that modulate cellular events, such as migration, invasion, and proliferation. During EVT differentiation, the expression of trophoblast integrin isoforms changes from a stationary phenotype (α6β4) to a more invasive state (α1β1). Here, irisin promoted integrin switching through the upregulation of α1 and the suppression of α6 integrin isomers. This process is necessary for proper uterine spiral artery remodeling during placentation to secure blood flow as gestation progresses. Failure of EVT differentiation and invasion accompanied by aberrant integrin switching is associated with adverse pregnancy outcomes, including preeclampsia and intrauterine growth restriction. The effect of irisin on integrin expression was described in a rat study where irisin improved endometrial receptivity by inducing the αvβ3 integrin.

These results show that pretreatment with the AMPK antagonist compound C abolishes the inhibitory effect of irisin on integrin α1 expression. The specific role of the AMPK pathway in the modulation of integrin switching in EVT differentiation is not well understood, however, a growing body of evidence shows AMPK signaling collectively controls integrin expression, internalization, and degradation.

Next, whether irisin also modulates villous trophoblast differentiation is evaluated. The above results show that irisin promotes syncytium formation and increases expression of the CTB differentiation marker GCM1. This multifunctional transcription factor is involved in STB formation, EVT invasion, and placental function by targeting key genes, including SYN1 (endogenous retrovirus group W member 1), placental growth factor, and high-temperature requirement protein A4. The dose-dependent increase in GCM1 expression induced by irisin is also accompanied by increased syncytium formation. In addition to promoting syncytium formation, irisin also induced PSG1. PSG1 is known for its role in the modulation of fetal tolerance by controlling the activation of T cells and the adaptation of the maternal innate immune system. Similar to its effects on EVTs, irisin induced CTB differentiation by activating the AMPK pathway, which has been shown to control trophoblast differentiation via the modulation of mitochondrial hemostasis and ATP coupling efficiency. Impaired trophoblast differentiation due to irregularities in placental AMPK activity was observed in pregnancy complications, such as GDM and preeclampsia. The AMPK pathway may be a therapeutic target in preeclampsia because of its activators that reduce disease symptoms. Here, it is shown that irisin improves the terminal differentiation of CTBs via an AMPK-dependent mechanism that improves mitochondrial and ATP homeostasis. This is consistent with a recent study where irisin improved mitochondrial function and cellular ATP biogenesis via AMPK-dependent mechanisms in cardiomyocytes.

This example provides the first mechanistic insights into the role of irisin in human trophoblast differentiation, which is abnormally regulated in placental insufficiency syndrome. As a naturally occurring molecule, irisin is a new target for the improvement of placental function.

Example 3

Placental hormones are vital to maintaining a healthy pregnancy, and altered levels of these hormones are associated with preeclampsia pathogenesis. Synthesizing key hormones and other mediators is a major placental function. Placental hormones are important throughout gestation, with key roles in pregnancy establishment and maintenance, fetal development and labor. Preeclampsia has been linked to pathologic alteration of several placental hormones including Pregnancy-Associated Plasma Protein-A (PAPP-A), human Chorionic Gonadotropin (hCG), Placental Growth Factor (PlGF), and Placental Protein 13 (PP13). Irisin, the secreted form of FNDC5, was first described in 2012 as a myokine polypeptide secreted from skeletal muscle that regulates glucose and lipid metabolism in adipose tissues. Later studies showed FNDC5/irisin is also expressed in adipose tissue, cardiomyocytes, the brain and other parts of the body. The variety of FNDC5/irisin expression patterns in these tissues suggests FNDC5/irisin may have other biological effects besides promoting energy metabolism. Using mass spectrometry, the following data shows for the first time that irisin is secreted by the human placenta (FIG. 12). Reduced expression of FNDC5 in placental protein extracts (FIG. 14A) and decreased irisin secretion from preeclampsia placentas compared to controls (FIG. 15) was also demonstrated. Clinical reports show irisin levels in the sera of preeclampsia patients are significantly reduced compared to women with healthy pregnancies.

Conflicting studies have questioned the role and presence of human irisin. Unfortunately, initial irisin studies used ELISA and performed poorly due to low antibody quality. It was also uncertain if FNDC5/irisin could be transcribed due to the alternative ATA start codon present in humans. These setbacks were overcome by new, more specific antibodies and alternative assays (e.g., mass spectrometry) that confirmed the presence of irisin in human circulation and its cellular function. Because the specificity of commercial anti-irisin antibodies is still controversial, to ensure rigorous results a custom polyclonal antibody (Ab) against FND5/irisin is designed and generated. The sensitivity and specificity of this antibody has been rigorously tested by ELISA and by using a blocking peptide. Data shows that the custom antibody detects FNDC5/irisin in the placenta with high specificity (FIG. 13), unlike commercial antibodies.

Using Western blots, it is found that FNDC5/irisin protein expression was decreased in preeclampsia placentas compared to healthy age-matched control placentas (FIG. 14A). Mass spectrometry is then used to measure irisin secretion in media from overnight cultured placental explants (FIG. 12) and a well over 90% decrease in irisin secreted into culture media from preeclampsia placentas is detected (FIG. 15). In addition, it is found that HIF1α overexpression in preeclampsia placentas coincides with downregulation of PGC1a (FIG. 16). It was also found that intracellular FNDC5 expression was strongly reduced in first-trimester placental tissue exposed to hypoxia (1.5% $pO_2$) for 16 hours (FIG. 14B). Irisin secretion into the culture media (ELISA) was also strongly reduced in hypoxic conditions compared to normoxia (FIG. 14C). This supports the notion that the transcription factor PGC1a regulates FNDC5/irisin expression and secretion in the human placenta via the HIF1α pathway (FIG. 17).

The question of whether irisin ameliorates the effects of oxidative stress in placenta via modulation of cellular antioxidants through the AMPK-NRF2 axis should also be considered. Oxidative stress during placental development is associated with pregnancy disorders including preeclampsia and intrauterine fetal growth restriction. Several studies show low 02 reduces placental expression and activities of antioxidants including catalase (CAT), superoxide dismutases (SODs), and glutathione peroxidase (GPx) and indicate that these reductions tightly correlate with preeclampsia pathophysiology. Increased oxidative stress leads to trophoblast apoptosis/necrosis and causes maternal endothelial dysfunction by altering the balance between pro- and anti-angiogenic factors. The nuclear factor Erythroid 2-Related Factor 2 (NRF2) is a transcription factor that plays a vital role in this process by interacting with antioxidant response elements (AREs) in promoter regions of a wide range of intracellular antioxidative proteins including CAT, SOD and GPx, and regulates their expression. NRF2 is reduced in preeclampsia placentas.

Further, irisin-regulated AMPK improves cell survival by promoting nuclear accumulation of NRF2 in HepG2 and HEK293 cells. An active form of NRF2 localizes to the nucleus and binds to AREs present in target genes, linking AMPK to NRF2 and antioxidative function. Irisin regulates glucose uptake in skeletal muscle cells via AMPK phosphorylation and similarly improves endothelial function in hypertensive rats. In human alveolar epithelial cells, irisin induces expression of NRF2 mRNA and protein. Irisin levels are lower in the peripheral circulation of preeclampsia mothers, but the role of irisin in placental function and/or its contribution to preeclampsia is unknown.

To test the cytoprotective property of irisin, first-trimester placental explants are exposed to hypoxia (1.5% $pO_2$) in absence or presence of 50 nM irisin. Irisin treatment significantly reduced apoptosis caused by hypoxia (FIGS. 18A-18C). Next, cultured HTR-8/SVneo cells in hypoxia (1.5% $pO_2$) were treated with 50 nM irisin. As a result, caspase-3 activity was inhibited (FIG. 19B) by reducing cytoplasmic interaction of APAF1 and cytochrome C, in turn interfering with apoptosome formation (FIG. 19A). Irisin treatment also increased phosphorylation of AMPK after 30 minutes and peaked after 1 hour (FIG. 20A). The mRNA expression of NRF2 (regulated by AMPK) and Glucose transporter type 4 (GLUT4), a down-stream gene controlled by irisin, were also increased in response to irisin treatment (FIG. 20B). These data support the notion that under oxidative stress conditions, irisin improves trophoblast survival by inducing NRF2 expression and nuclear translocation through AMPK to promote intracellular antioxidant protein expression (FIG. 21).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of treating a subject having a placental dysfunction, the method comprising:
   administering to the subject a therapeutically effective amount of a composition comprising irisin.

2. The method according to claim 1, wherein the administering is performed orally, sublingually, intravenously, intramuscularly, intravaginally, subcutaneously, or directly to the placenta of the subject.

3. The method according to claim 1, wherein the placental dysfunction is preeclampsia, oligohydramnios, intrauterine growth restriction, abnormal placental growth, abnormal angiogenesis, abnormal apoptosis, abnormal oxidative stress, or combinations thereof.

4. The method according to claim 1, wherein the irisin is recombinant irisin and wherein the recombinant irisin optionally includes a tag.

5. The method according to claim 1, wherein the irisin is purified from a fluid or a tissue from a human or non-human mammal.

6. The method according to claim 1, wherein the composition further comprises a pharmaceutically acceptable carrier.

7. The method according to claim 1, wherein the placental dysfunction is preeclampsia and the method further comprises:
   administering a therapeutically effective amount of an antihypertensive agent to the subject.

8. The method according to claim 1, wherein the subject is a human or non-human mammal.

9. A method of treating a subject suspected of having a placental dysfunction, the method comprising:
   obtaining a plurality of cells originating from the subject's placenta or cervix;
   determining a first irisin level expressed from the plurality of cells;
   comparing the first irisin level with a second irisin level provided from a normal control; and
   when the first irisin level is lower than the second irisin level, administering to the subject a therapeutically effective amount of a composition comprising irisin.

10. The method according to claim 9, wherein the normal control comprises a second plurality of cells originating from a different placenta or cervix of the same subject from a previous pregnancy at a corresponding gestation time.

11. The method according to claim 9, wherein the normal control comprises a second plurality of cells originating from a placenta or cervix of a different subject or plurality of subjects at a corresponding gestation time.

12. The method according to claim 9, wherein the administering is performed when the first irisin level is at least about 20% lower than the second irisin level.

13. The method according to claim 9, wherein the administering is performed orally, sublingually, intravenously, intramuscularly, intravaginally, subcutaneously, or directly to the placenta of the subject.

14. A method of treating a placenta by increasing trophoblast differentiation, increasing placental outgrowth, decreasing trophoblast apoptosis, decreasing oxidative stress, or a combination thereof, the method comprising:
   contacting the placenta with irisin; and wherein the contacting the placenta with irisin results from administering a composition comprising the irisin to a human or non-human mammalian subject.

15. The method according to claim 14, wherein the human or non-human mammalian subject has a placental dysfunction.

16. The method according to claim 15, wherein the placental dysfunction is oligohydramnios, intrauterine growth restriction, abnormal placental growth, abnormal angiogenesis, abnormal apoptosis, abnormal oxidative stress, or a combination thereof.

17. The method according to claim 15, wherein the placental dysfunction is preeclampsia.

18. The method according to claim 14, wherein the administering is performed orally, sublingually, intravenously, intramuscularly, intravaginally, subcutaneously, or directly to the placenta of the subject.

19. The method according to claim 14, wherein the irisin is delivered to the placenta through an artery.

\* \* \* \* \*

SEQUENCE LISTING

<160> NUMBER OF SEQ ID NOS: 7

<210> SEQ ID NO 1
<211> LENGTH: 212
<212> TYPE: PRT
<213> ORGANISM: Homo sapiens

<400> SEQUENCE: 1

Met His Pro Gly Ser Pro Ser Ala Trp Pro Pro Arg Ala Arg Ala Ala
1               5                   10                  15

Leu Arg Leu Trp Leu Gly Cys Val Cys Phe Ala Leu Val Gln Ala Asp
            20                  25                  30

Ser Pro Ser Ala Pro Val Asn Val Thr Val Arg His Leu Lys Ala Asn
        35                  40                  45

Ser Ala Val Val Ser Trp Asp Val Leu Glu Asp Glu Val Val Ile Gly
    50                  55                  60

Phe Ala Ile Ser Gln Gln Lys Lys Asp Val Arg Met Leu Arg Phe Ile
65                  70                  75                  80

Gln Glu Val Asn Thr Thr Thr Arg Ser Cys Ala Leu Trp Asp Leu Glu
                85                  90                  95

Glu Asp Thr Glu Tyr Ile Val His Val Gln Ala Ile Ser Ile Gln Gly
            100                 105                 110

Gln Ser Pro Ala Ser Glu Pro Val Leu Phe Lys Thr Pro Arg Glu Ala
        115                 120                 125

Glu Lys Met Ala Ser Lys Asn Lys Asp Glu Val Thr Met Lys Glu Met
    130                 135                 140

Gly Arg Asn Gln Gln Leu Arg Thr Gly Glu Val Leu Ile Ile Val Val
145                 150                 155                 160

Val Leu Phe Met Trp Ala Gly Val Ile Ala Leu Phe Cys Arg Gln Tyr
                165                 170                 175

Asp Ile Ile Lys Asp Asn Glu Pro Asn Asn Asn Lys Glu Lys Thr Lys
            180                 185                 190

Ser Ala Ser Glu Thr Ser Thr Pro Glu His Gln Gly Gly Gly Leu Leu
        195                 200                 205

Arg Ser Lys Ile
    210

<210> SEQ ID NO 2
<211> LENGTH: 31
<212> TYPE: PRT
<213> ORGANISM: Artificial Sequence
<220> FEATURE:
<223> OTHER INFORMATION: FNDC5 signal sequence

<400> SEQUENCE: 2

Met His Pro Gly Ser Pro Ser Ala Trp Pro Pro Arg Ala Arg Ala Ala
1               5                   10                  15

Leu Arg Leu Trp Leu Gly Cys Val Cys Phe Ala Leu Val Gln Ala
            20                  25                  30

<210> SEQ ID NO 3
<211> LENGTH: 112
<212> TYPE: PRT
<213> ORGANISM: Artificial Sequence
<220> FEATURE:
<223> OTHER INFORMATION: irisin

<400> SEQUENCE: 3

Asp Ser Pro Ser Ala Pro Val Asn Val Thr Val Arg His Leu Lys Ala

```
                1               5                   10                  15
Asn Ser Ala Val Val Ser Trp Asp Val Leu Glu Asp Glu Val Ile
            20                  25                  30

Gly Phe Ala Ile Ser Gln Gln Lys Lys Asp Val Arg Met Leu Arg Phe
            35                  40                  45

Ile Gln Glu Val Asn Thr Thr Thr Arg Ser Cys Ala Leu Trp Asp Leu
50                  55                      60

Glu Glu Asp Thr Glu Tyr Ile Val His Val Gln Ala Ile Ser Ile Gln
65                  70                  75                  80

Gly Gln Ser Pro Ala Ser Glu Pro Val Leu Phe Lys Thr Pro Arg Glu
                85                  90                  95

Ala Glu Lys Met Ala Ser Lys Asn Lys Asp Glu Val Thr Met Lys Glu
                100                 105                 110

<210> SEQ ID NO 4
<211> LENGTH: 9
<212> TYPE: PRT
<213> ORGANISM: Artificial Sequence
<220> FEATURE:
<223> OTHER INFORMATION: FNDC5 spacer

<400> SEQUENCE: 4

Met Gly Arg Asn Gln Gln Leu Arg Thr
1               5

<210> SEQ ID NO 5
<211> LENGTH: 21
<212> TYPE: PRT
<213> ORGANISM: Artificial Sequence
<220> FEATURE:
<223> OTHER INFORMATION: FNDC5 transmembrane region

<400> SEQUENCE: 5

Gly Glu Val Leu Ile Ile Val Val Val Leu Phe Met Trp Ala Gly Val
1               5                   10                  15

Ile Ala Leu Phe Cys
            20

<210> SEQ ID NO 6
<211> LENGTH: 39
<212> TYPE: PRT
<213> ORGANISM: Artificial Sequence
<220> FEATURE:
<223> OTHER INFORMATION: FNDC5 cytoplasmic domain

<400> SEQUENCE: 6

Arg Gln Tyr Asp Ile Ile Lys Asp Asn Glu Pro Asn Asn Lys Glu
1               5                   10                  15

Lys Thr Lys Ser Ala Ser Glu Thr Ser Thr Pro Glu His Gln Gly Gly
            20                  25                  30

Gly Leu Leu Arg Ser Lys Ile
        35

<210> SEQ ID NO 7
<211> LENGTH: 25
<212> TYPE: PRT
<213> ORGANISM: Artificial Sequence
<220> FEATURE:
<223> OTHER INFORMATION: irisin peptide

<400> SEQUENCE: 7

Ala Asn Ser Ala Val Val Ser Trp Asp Val Leu Glu Asp Glu Val Val
```

-continued

```
1               5               10              15
Ile Gly Phe Ala Ile Ser Gln Gln Lys
                20              25
```